United States Patent
Arnold et al.

(10) Patent No.: US 8,519,210 B2
(45) Date of Patent: Aug. 27, 2013

(54) PROCESS FOR PRODUCING ETHYLENE VIA OXIDATIVE DEHYDROGENATION (ODH) OF ETHANE

(75) Inventors: Stephen Craig Arnold, Mountain Lakes, NJ (US); Anne Mae Gaffney, West Chester, PA (US); Ruozhi Song, Wilmington, DE (US); Chuen Yuan Yeh, Edison, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 246 days.

(21) Appl. No.: 12/417,523

(22) Filed: Apr. 2, 2009

(65) Prior Publication Data

US 2010/0256432 A1    Oct. 7, 2010

(51) Int. Cl.
*C07C 5/333* (2006.01)

(52) U.S. Cl.
USPC ............ 585/663; 585/661; 585/662; 585/655

(58) Field of Classification Search
USPC ................. 585/661, 662, 663, 655, 654, 658; 502/305, 311, 312
See application file for complete search history.

(56) References Cited

U.S. PATENT DOCUMENTS

| | | | |
|---|---|---|---|
| 4,250,346 A | 2/1981 | Young et al. | |
| 4,299,800 A | 11/1981 | Nishikawa et al. | |
| 4,524,236 A * | 6/1985 | McCain | 585/658 |
| 4,940,826 A | 7/1990 | Font Freide et al. | |
| 4,990,632 A * | 2/1991 | Ramachandran et al. | 549/523 |
| 5,157,204 A | 10/1992 | Brown et al. | |
| 5,446,232 A | 8/1995 | Chen et al. | |
| 6,433,234 B1 | 8/2002 | Griffiths et al. | |
| 6,518,476 B1 * | 2/2003 | Culp et al. | 585/655 |
| 6,566,573 B1 | 5/2003 | Bharadwaj et al. | |
| 6,747,066 B2 | 6/2004 | Wang et al. | |
| 6,841,699 B2 * | 1/2005 | Bogan et al. | 562/547 |
| 6,858,768 B2 | 2/2005 | Budin et al. | |
| 7,135,603 B2 * | 11/2006 | Messenger | 585/324 |

(Continued)

FOREIGN PATENT DOCUMENTS

JP    07-053414    2/1995

OTHER PUBLICATIONS

English Patent Abstract of JP07-053414 from esp@cenet, Ushikubo et al., published Feb. 28, 1995, 1 page.

(Continued)

*Primary Examiner* — In Suk Bullock
*Assistant Examiner* — Bradley Etherton
(74) *Attorney, Agent, or Firm* — Alix, Yale & Ristas, LLP

(57) ABSTRACT

A process for the oxidative dehydrogenation of ethane is disclosed. The process may include: contacting an ethane feed and an oxygen-containing gas in the presence of an oxidative dehydrogenation catalyst in an oxidative dehydrogenation reaction zone under conditions to oxidatively dehydrogenate at least a portion of the ethane to produce a product stream comprising ethylene, carbon oxides, water, and unreacted oxygen and ethane, wherein an oxygen concentration in the product stream is at least 0.1 mol %; contacting the product stream with an oxygen elimination catalyst in an oxygen elimination reaction zone to combust at least a portion of the oxygen; recovering from the oxygen elimination reaction zone an effluent having a reduced oxygen content; separating water from the effluent; separating carbon oxides and any non-condensable gas(es) from the ethylene and the unreacted ethane; and separating the ethylene from the unreacted ethane.

15 Claims, 7 Drawing Sheets

(56) References Cited

U.S. PATENT DOCUMENTS

| | | | |
|---|---|---|---|
| 7,319,179 B2* | 1/2008 | Lopez Nieto et al. | 585/658 |
| 2002/0161256 A1* | 10/2002 | Bogan et al. | 558/320 |
| 2005/0085678 A1 | 4/2005 | Lopez Nieto et al. | |

OTHER PUBLICATIONS

International Search Report and Written Opinion of the International Searching Authority, International Patent Application No. PCT/US10/29789, mailed Jun. 11, 2010.

Selective Oxidative Dehydrogenation of Ethane on Mo VTeNbO Mixed Metal Oxide Catalysts: by P. Botella, E. Garcia-Gonzalez, A. Dejoz, J.M. Lopes Nieto, M.I. Vazquez, and J. Gonzalez-Calbet, Journal of Catalysis 225, pp. 428-438, May 28, 2004.

Preparation of MoVTe(Sb)Nb Mixed Oxide Catalysts Using a Slurry Method for Selective Oxidative Dehydrogenation of Ethane: by Q.Xie, L. Chen, W. Weng, and H. Wan, Journal of Molecular Catalysis A. 240: 191-196, 2005.

Kinetics of Oxidative Dehydrogenation of C2-C3 Alkanes on Oxide Catalysts: by Grabowski, R., Catalysis Reviews, Science and Engineering 48, pp. 199-268, 2006.

* cited by examiner

PROCESS FOR PRODUCING ETHYLENE VIA OXIDATIVE DEHYDROGENATION (ODH) OF ETHANE

BACKGROUND OF DISCLOSURE

1. Field of the Disclosure

Embodiments disclosed herein relate generally to a process for the oxidative dehydrogenation of hydrocarbons to form olefins. More specifically, embodiments disclosed herein relate to a process for the oxidative dehydrogenation of ethane to form ethylene. Such processes may be performed in the presence of a mixed metal oxide catalyst, allowing for exceptionally high selectivity to the olefin at all hydrocarbon conversion levels (from <20% to >90%).

2. Background

Ethylene is an important petrochemical used as a raw material for the manufacture of polymers, ethylbenzene, styrene, and polystyrene, among other chemical products. Over 90% of currently produced ethylene is derived from steam cracking of naphtha and/or ethane and/or propane. Ethylene may be obtained from the non-catalytic thermal cracking of saturated hydrocarbons, such as ethane and propane, and alternatively from thermal or steam cracking of heavier liquids such as naphtha and gas oil. Steam cracking produces a variety of other products, including diolefins and acetylene. The latter are costly to separate from the ethylene, usually by extractive distillation and/or selective hydrogenation to the corresponding mono-olefin, e.g. acetylene to ethylene. An ethylene plant using thermal cracking typically achieves an ethylene selectivity up to 80-85 percent calculated on a carbon atom basis at an ethane conversion of 55-65 percent. In addition, thermal cracking processes for olefin production are highly endothermic. Accordingly, these processes require a large consumption of fuel and the construction and maintenance of large, capital-intensive and complex cracking furnaces to supply the heat.

Existing steam cracking processes generate ethylene by raising the feed (ethane or other hydrocarbons) to high enough temperature (700-1000° C.) in furnace tubes to thermally crack the hydrocarbons into olefins, especially ethylene and secondarily propylene, plus a range of other hydrocarbons, hydrogen and coke. The residence time must be very short, at a level measured in milliseconds, and the effluent must be quenched immediately, in order to maximize the desired olefins and minimize the undesired by-products. The pressure must be kept to a minimum, substantial steam dilution is required, and design features are critical for obtaining the best performance. As a result, the reaction conditions are very sensitive, and the furnaces are very expensive, with high fuel requirement due to both the high temperature and the high endothermicity of the cracking reactions. Frequent decoking is also a major requirement. Furthermore, furnace tubes must be replaced periodically.

Autothermal cracking ("ATC") is a similar process, but with a combustion reaction added to supply the heat, as an alternative to using expensive heat transfer in furnaces. The combustion reaction may include use of a catalyst, for which the high temperature and other conditions are a severe environment. There are still very sensitive cracking reactions and quenching, with a range of products, and the added combustion reactions create additional byproducts while consuming either a portion of the feed and product and/or a combustible that is added.

An alternative is to catalytically dehydrogenate ethane in the presence of oxygen to form ethylene. The process is called oxidative dehydrogenation (ODH). In this process, the product is largely limited to ethylene with small amounts of carbon monoxide and carbon dioxide as byproducts. The effluent also contains water (produced in the reaction plus whatever enters with the feed), residual ethane, some residual oxygen, and nitrogen if introduced with the oxygen (e.g., as air). The oxidative dehydrogenation (ODH) of ethane is thermodynamically favored and can be carried out at lower reaction temperatures without coke formation.

In U.S. Pat. No. 4,250,346, ethane is catalytically oxydehydrogenated to ethylene in a gas phase reaction, in the presence or absence of water, at temperatures of less than 550° C. The catalysts disclosed include oxides of molybdenum: $Mo_aX_bY_c$, where X=Cr, Mn, Nb, Ta, Ti, V and/or W, Y=Bi, Ce, Co, Cu, Fe, K, Mg, Ni, P, Pb, Sb, Si, Sn, Tl and/or U.

U.S. Pat. No. 4,524,236 discloses catalysts useful for the production of ethylene from ethane via oxidative dehydrogenation, including oxides of molybdenum: $Mo_aV_bNb_cSb_dX_e$, where X=Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W. The reaction can be carried out in the presence or absence of water; however, significant amounts of acetic acid are formed in the presence of water, which results in reduced ethylene selectivity.

U.S. Pat. No. 6,858,768 discloses catalysts useful for the production of olefins from alkanes via oxidative dehydrogenation, including an oxide selected from the group containing alumina, zirconia, titania, ytria, silica, niobia, and vanadia. As disclosed, the catalysts need substantially elevated temperatures for activation.

U.S. Pat. No. 7,319,179 discloses mixed metal oxide catalysts comprising molybdenum, vanadium, tellurium, and niobium useful as a catalyst for ODH of ethane to ethylene.

JP 07-053414 discloses use of mixed metal oxide catalysts containing transition metal elements with molybdenum, vanadium, niobium, and tellurium for the ODH of ethane to ethylene. The best selectivity reported therein is 91.5 C % ethylene at 56.7% conversion at a reaction temperature of 360° C.

Other patents discussing ODH of ethane to ethylene include U.S. Pat. Nos. 6,858,768, 7,135,603, 4,940,826, 6,433,234, and 6,566,573. Various other references discussing ODH include: P. Botella, E. Garcia-Gonzalez, A. Dejoz, J. M. Lopez-Nieto, M. I. Vazquez, and J. Gonzalez-Calbet, "Selective oxidative dehydrogenation of ethane on MoVTeNbO mixed metal oxide catalysts," *Journal of Catalysis* 225: 428-438, 2004; Q. Xie, L. Chen, W. Weng, and H. Wan "Preparation of MoVTe(Sb)Nb mixed oxide catalysts using a slurry method for selective oxidative dehydrogenation of ethane," *Journal of Molecular Catalysis A*. 240: 191-196, 2005; and Grabowski, R. "Kinetics of oxidative dehydrogenation of C2-C3 alkanes on oxide catalysts," *Catal. Rev. Sci and Eng'g*. 48: 199-268, 2006.

Due to the potential advantages over the prior art, ODH of ethane to ethylene has been the object of considerable research. Over the years, many catalyst systems have been investigated, including carbon molecular sieves, metal phosphates, and mixed metal oxides. However, commercialization has not been possible due to low product selectivity at reasonably high ethane conversions. In many of the prior art processes using ODH to form ethylene, the oxygen has generated excessive byproducts (primarily COx), with selectivity to the desired ethylene product reaching no higher than 80-85 C % at ethane conversion of 55-65%. At this level of selectivity and conversion, no advantage over steam cracking is realized, especially as the primary by-products ($CO_x$) do not provide added value, in contrast to significant value for the hydrocarbon byproducts from steam cracking.

Accordingly, there remains a need in the art for ODH processes having high selectivity at reasonably high hydrocarbon conversions.

SUMMARY OF THE DISCLOSURE

In one aspect, embodiments disclosed herein relate to a process for the oxidative dehydrogenation of ethane to ethylene, including: contacting an ethane feed and an oxygen-containing gas in the presence of an oxidative dehydrogenation catalyst in an oxidative dehydrogenation reaction zone under conditions to oxidatively dehydrogenate at least a portion of the ethane to produce a product stream comprising ethylene, carbon oxides, water, and unreacted oxygen and ethane, wherein an oxygen concentration in the product stream is at least 0.1 mol %; contacting the product stream with an oxygen elimination catalyst in an oxygen elimination reaction zone to combust at least a portion of the oxygen; recovering from the oxygen elimination reaction zone an effluent having a reduced oxygen content; separating water from the effluent; separating carbon oxides and any non-condensable gas(es) from the ethylene and the unreacted ethane; and separating the ethylene from the unreacted ethane.

In another aspect, embodiments disclosed herein relate to a process for the oxidative dehydrogenation of ethane to ethylene, including: contacting ethane and an oxygen-containing gas in the presence of a multi metal-oxide catalyst in an oxidative dehydrogenation reactor under conditions to oxidatively dehydrogenate at least a portion of the ethane to produce a product stream comprising ethylene, carbon oxides, water, and unreacted ethane; separating water from the product stream to recover a water fraction and a fraction comprising carbon oxides, ethylene and unreacted ethane; separating the fraction comprising carbon oxides, ethylene and unreacted ethane to recover carbon oxides and any non-condensable gas(es) and a hydrocarbon fraction comprising ethylene and unreacted ethane; and separating the hydrocarbon fraction comprising ethylene and unreacted ethane to form an ethylene fraction and an ethane fraction; wherein the multi-metal-oxide catalyst comprises at least one catalyst selected from the group consisting of:

a) $MO_aV_bNb_cTe_eO_n$
wherein for catalyst a), a=1.0; b=0.05 to 1.0, c=0.001 to 1.0, e=0.001 to 0.5, and n is determined by the oxidation states of the other elements;

b) $MO_aV_bX_cY_dZ_eO_n$;
wherein for catalyst b), X=at least one of Nb and Ta; Y=at least one of Sb and Ni; Z=at least one of the Te, Ga, Pd, W, Bi and Al; a=1.0; b=0.05 to 1.0; c=0.001 to 1.0; d=0.001 to 1.0; e=0.001 to 0.5; and n is determined by the oxidation states of the other elements; and c) $MO_aV_bX_cY_dZ_eM_fO_n$,
wherein for catalyst c), X=at least one of Nb and Ta; Y=at least one of Sb and Ni; Z=at least of one of Te, Ga, Pd, W, Bi and Al; M=at least one of Fe, Co, Cu, Cr, Ti, Ce, Zr, Mn, Pb, Mg, Sn, Pt, Si, La, K, Ag and In; a=1.0; b=0.05 to 1.0; c=0.001 to 1.0; d=0.001 to 1.0; e=0.001 to 0.5; and f=0.001 to 0.3; and n is determined by the oxidation states of the other elements.

Other aspects and advantages will be apparent from the following description and the appended claims.

DETAILED DESCRIPTION

Figure 1:
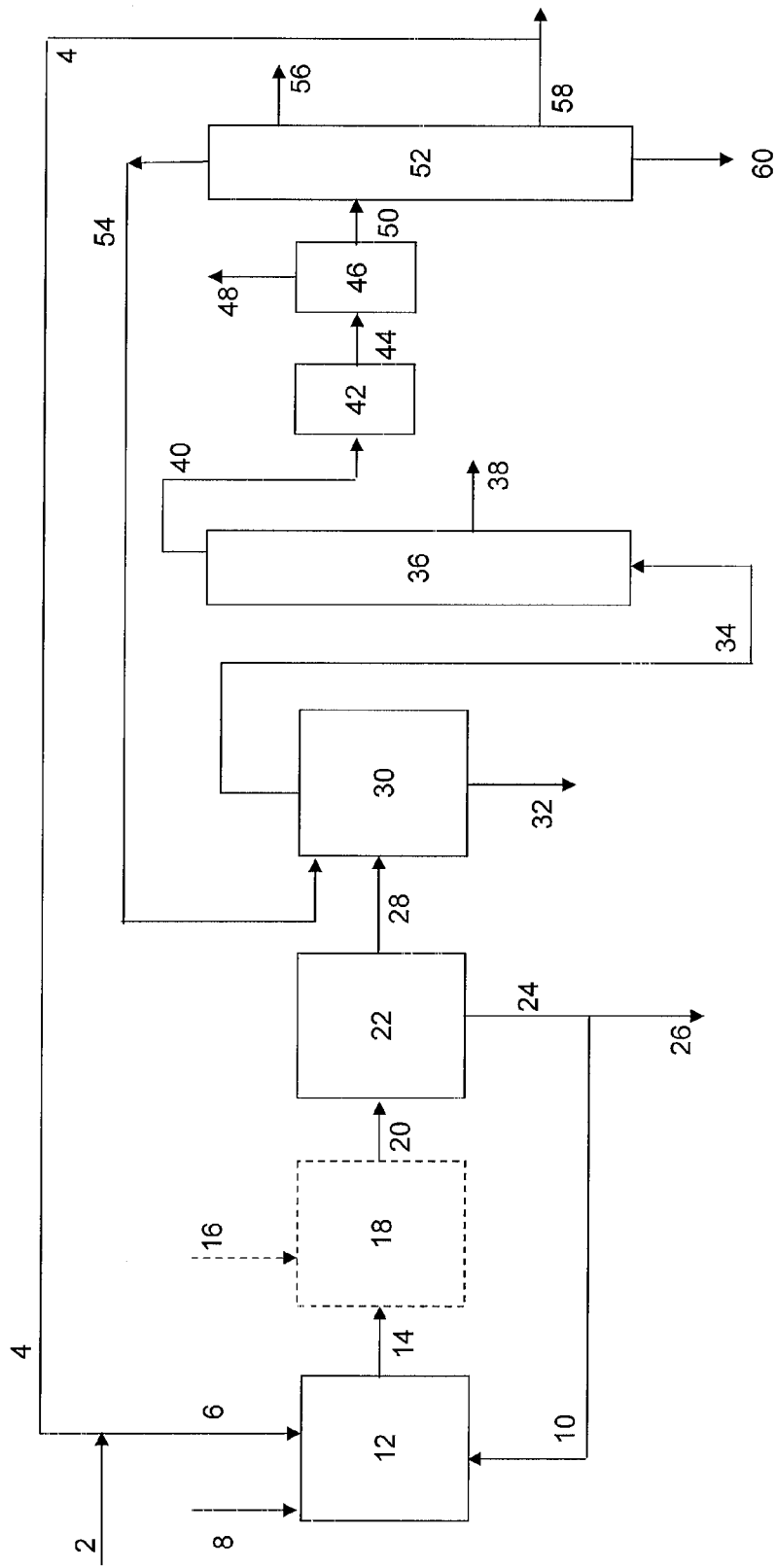
FIG. 1 is a simplified process flow diagram for oxidative dehydrogenation processes according to embodiments disclosed herein.

In one aspect, embodiments herein relate to a process for the oxidative dehydrogenation of hydrocarbons to form olefins. More specifically, embodiments disclosed herein relate to a process for the oxidative dehydrogenation of ethane to form ethylene. Such processes may be performed in the presence of a mixed metal oxide catalyst, allowing for exceptionally high selectivity to the olefin at all hydrocarbon conversion levels (e.g., from <20% to >90%). In some embodiments, essentially no hydrocarbon byproducts and minimal amounts of carbon oxides are produced.

Oxidative dehydrogenation (ODH) processes according to embodiments disclosed herein may be performed by contacting a hydrocarbon and an oxygen containing gas in the presence of a multi-metal oxide catalyst under conditions to oxidatively dehydrogenate at least a portion of the hydrocarbon to produce an olefin product. The multi-metal-oxide catalysts disclosed hereinbelow and in U.S. patent application Ser. No. 12/417,488, titled "Process for Making Catalysts Useful for the Conversion of Paraffins to Olefins," and Ser. No. 12/417,507, titled "Catalysts for the Conversion of Paraffins to Olefins and Use Thereof," each filed of even date herewith, and incorporated herein by reference, is prepared in a manner such that the resulting catalyst has an exceptionally high selectivity toward olefin production, at all hydrocarbon conversion levels. The catalysts described herein, together with the reactor conditions reflected herein, result in high enough ethylene selectivity and ethane conversion to provide an economical process for ODH of ethane to ethylene.

ODH processes disclosed herein, when used with catalysts prepared according to embodiments disclosed herein for ODH of a ethane to ethylene, may have an ethylene selectivity of at least 85 mole % at an ethane conversion of at least 60%. In some embodiments, processes disclosed herein may have an ethylene selectivity of at least 88 mole % at an ethane conversion of at least 60%; an ethylene selectivity of at least 90 mole % at an ethane conversion of at least 60% in other embodiments; in other embodiments, catalysts disclosed herein may have an ethylene selectivity of at least 90 mole % at an ethane conversion of at least 65%; an ethylene selectivity of at least 90 mole % at an ethane conversion of at least 70% in other embodiments; and an ethylene selectivity of at least 90 mole % at an ethane conversion of at least 75% in yet other embodiments.

For example, when used for the oxidative dehydrogenation of ethane to ethylene, processes disclosed herein may have an ethylene selectivity of at least 97.5 wt. % carbon ("C %") at an ethane conversion below 20%. In some embodiments, processes disclosed herein may have an ethylene selectivity of at least 97 C % at an ethane conversion of about 20-30%; an ethylene selectivity of at least 96 C % at an ethane conversion of about 30-40% in other embodiments; in other embodiments, catalysts disclosed herein may have an ethylene selectivity of at least 95 C % at an ethane conversion of about 40-50%;

an ethylene selectivity of at least 93.5 C % at an ethane conversion of about 50-60%. in other embodiments; at least 91 C % at an ethane conversion of about 60-70%, at least 88 C % at an ethane conversion of about 70-80%, and an ethylene selectivity of at least 84 C % at an ethane conversion of about 80-90% in yet other embodiments. The catalysts and the ODH processes of embodiments disclosed herein are described in more detail below.

Catalyst

Catalysts useful in ODH processes disclosed herein may include at least one of:
a) $Mo_aV_bNb_cTe_eO_n$;
b) $Mo_aV_bX_cY_dZ_eO_n$; and
c) $Mo_aV_bX_cY_dZ_eM_fO_n$.

For catalyst a), a=1.0; b=0.05 to 1.0, c=0.001 to 1.0, e=0.001 to 0.5, and n is determined by the oxidation states of the other elements. For catalyst b), X=at least one of Nb and Ta; Y=at least one of Sb and Ni; Z=at least one of the Te, Ga, Pd, W, Bi and Al; a=1.0 (normalized); b=0.05 to 1.0; c=0.001 to 1.0; d=0.001 to 1.0; e=0.5; and n is determined by the oxidation states of the other elements. For catalyst c), X=at least one of Nb and Ta; Y=at least one of Sb and Ni; Z=at least of one of the Te, Ga, Pd, W, Bi and Al; M=at least one of Fe, Co, Cu, Cr, Ti, Ce, Zr, Mn, Pb, Mg, Sn, Pt, Si, La, K, Ag and In; a=1.0 (normalized) ; b=0.05 to 1.0; c=0.001 to 1.0; d=0.001 to 1.0; e=0.001 to 0.5; and f=0.001 to 0.3; and n is determined by the oxidation states of the other elements.

It has surprisingly been found by the present inventors that the above catalysts may provide for the desired improvements in selectivity and conversion when prepared in accordance with preparation methods disclosed herein. Other catalysts compositions, such as those disclosed in JP 07-053414, U.S. Pat. Nos. 4,524,236, and 7,319,179, may also be used, so long as the catalyst compositions are prepared in accordance with procedures disclosed herein. Each of these is incorporated herein to the extent not contradictory with catalyst preparation methods disclosed herein.

The above described catalysts may be prepared by a process including at least the following steps. In a first step, compounds of the different metals, or pure elements, or of a mixture of both may be admixed. The admixing may be performed starting from the compounds of the different elements, starting from the actual pure elements in solution, or by hydrothermal methods.

The elements Mo, V, Nb, Sb, and Te can be incorporated into the admixing step as pure metallic elements, as salts, as oxides, as hydroxides, as alkoxides, as acids, or as mixtures of two or more of the above-mentioned forms. As salts, sulfates, nitrates, oxalates, halides, or oxyhalides may be used. For example, the Mo can be incorporated at the mixing stage as molybdic acid, ammonium heptamolybdate, molybdenum chlorides, molybdenum acetate, molybdenum ethoxide and/or molybdenum oxides. The V can be incorporated at the admixing step, for example, as ammonium vanadate, vanadium oxide, vanadyl sulfate, vanadyl oxalate, vanadium chloride or vanadyl trichloride. The Nb can be incorporated at the admixing step, for example, as niobium pentoxide, niobium oxalate, niobium chloride or Nb metal. The Sb can be incorporated at the admixing step, for example, as antimony oxalate, antimony oxide, antimony chloride and antimony acetate. The Te can be incorporated at the admixing step, for example, as telluric acid, tellurium dioxide, tellurium ethoxide, tellurium chloride and metallic tellurium.

The elements Ta, Ni, Pd, W, Ga, Al, Cu, Bi, Sn, Fe, Co, rare earth, alkaline metals or alkaline earth metals may also be incorporated at the admixing step as salts, oxides, hydroxides or alkoxides, pure or as mixtures of two or more elements. In some embodiments, they may be incorporated as sulfates, nitrates, oxalates or halides.

The above elements and compounds may be combined to form one or more solutions or slurries, which may be subsequently admixed.

Nitric acid is used to adjust the pH of the resulting admixture or an initial admixture to be combined with additional solutions or slurries to form the desired catalyst composition. For example, in some embodiments, a solution including all desired compounds may be formed and the pH adjusted using nitric acid. As another example, in some embodiments, a first solution may be formed including a subset of the desired compounds, and a second solution may be formed including a subset of the remaining compounds; the first or second solution may then be mixed with nitric acid and the first and second solutions then admixed to result in the desired catalyst composition.

The admixing step may be followed by a period of static permanence in the reactor, or the mixing may be carried out with stirring. Both the static permanence and the stirring may be done in a normal reactor or in an autoclave. The admixing step may be carried out in solution, such as in deionized water, or by means of hydrothermal treatment.

The resulting admixture may then be dried. Drying may be carried out by conventional methods in a kiln, evaporation with stirring, and evaporation in a rotavapor, by spray drying, or by vacuum drying, among other methods.

The dried solids may then be calcined. Calcination of the dry solid can be carried out in an inert gas atmosphere, such as for example nitrogen, helium, argon or mixtures, of air or mixtures.

An alternative embodiment of the method is, as stated earlier, carried out by employing hydrothermal methods (containing two or more elements in the synthesis, especially containing Mo, V, Te, Sb, and Nb). The synthesis temperature and time may be determining conditions used during hydrothermal methods. The synthesis temperature may be within the range from about 100° C. to about 250° C. in some embodiments, and from about 150° C. to about 200° C. in other embodiments. The synthesis time may be within the range from about 6 to about 500 hours in some embodiments, and from about 24 to about 200 hours in other embodiments.

Calcination may be carried out by causing a flow of inert gas to pass (with spatial velocities between 1 and 400 $h^{-1}$) or statically. Calcination temperatures may range from about 250° C. to about 1000° C. in some embodiments, and from about 400° C. to about 800° C. in other embodiments. The calcination time is not a determining factor, though calcination times may range from about 0.5 hours to about 20 hours. The speed of heating is not a determining factor, though between 0.1° C./minute to about 10° C./minute is typical. The catalyst may also be initially calcined in an oxidizing atmosphere at a temperature up to about 350° C. in some embodiments, and within the range from about 250° C. to about 300° C. in other embodiments, and later be subjected to calcination in an inert atmosphere.

Various elements, such as Ta, Ni, Pd, W, Ga, Al, Cu, Bi, Sn, Fe, Co, rare earth, alkaline metals or alkaline earth metals may also be incorporated after the calcination stage by impregnation or precipitation. In this case, the resulting solid will be subjected to a second calcination stage.

The resulting solid formed by the above described methods may then be sized and formed into a desired catalyst particle.

Sizing may include grinding of the solids to form a powder. The resulting powder may then be pressed and sized to form, for example, granules. In some embodiments, the granules are formed to be within the 12-20 mesh size range.

Grinding is an important step in embodiments disclosed herein, not only for forming the desired catalyst particle, but also for the improvement of catalyst performance, including activity and ethylene selectivity. There is no particular restriction as to the grinding method. It can be conventional methods, for example, drying milling, wet milling, cryogenic milling and jet milling. Preferred BET surface area after grinding is in the range of 5-30 $m^2/g$ and 8-20 $m^2/g$ is more preferred. The ground catalyst powder can be used for the following purposes:

1. Size to desired particle for performance evaluation in a lab-scale reactor
2. Shape to desired form and size for commercial application such as forming extrudate, pellet or wash-coated onto pre-shaped supports.
3. Use for post treatment such as acid treatment for further improved performance. After acid treatment, the catalyst powder can then be sized for performance evaluation in lab or shaped to desired form and size for commercial application.

In other embodiments, the above catalysts may be formed on a support. Suitable supports for the catalyst include silica, alumina, silica-aluminas, aluminosilicates, zirconia, titania, boria, zirconia toughened alumina, lithium aluminum silicates, silicon carbide, oxide-bonded silicon carbide, and mixtures thereof. When used on a support, the supported catalyst usually comprises from about 10 to 50% by weight of the catalyst composition, with the remainder being the support. When the catalyst is to be used with a support, in some embodiments it is desirable to filter the combined solution to remove the insoluble portion before impregnating the support.

In other embodiments, catalysts formed according to the processes described above may undergo one or more acid treatment and/or annealing stages. For example, calcined catalysts or sized catalysts particles may be contacted with a carboxylic acid, such as oxalic acid. In some embodiments, the acid treatment can be carried out with the calcined and ground powder and followed by catalyst shaping. In other embodiments, the acid used for the treatment can be mineral acids, such as nitric acid, sulfuric acid and phosphoric acid. The acid concentration used for treatment according to embodiments disclosed herein may be within the range from about 0.5% to about 40%; from about 1% to about 20% in other embodiments. Acid treatment temperatures may be within the range from about 20 to about 150° C. in some embodiments, and from about 50 to about 120° C. in other embodiments. The resulting solids may then be dried and sized, if necessary. If necessary, annealing, for example, may be performed by heating the acid-treated catalyst to a temperature in the range of 300° C. to about 500° C., such as about 400° C., for a time period of at least 1 hour.

Powder catalyst obtained as described above may be formed into extrudates in some embodiments. For example, a powder catalyst may be mixed with a binder, such as silica or other binders known to one skilled in the art. The mixture may then be extruded, such as with a Loomis Ram Extruder or other suitable equipment, to form extrudates of the desired size. The extrudates may then be dried in an oven at temperatures in the range from about 100° C. to about 150° C., and may then be calcined at temperatures from about 250° C. to about 700° C.

In addition to extrudates, the catalyst may also be formed into other various shapes in combination with a binder. For example, catalyst pellets may be prepared by mixing catalyst powder with a binder and/or pre-shaped supports by wash-coating. Other useful catalyst shapes may include spheres, rings, and tri-lobed or other various shapes known to those skilled in the art. Catalysts used herein may additionally be suitably manufactured for use in fluidized bed reactors.

Oxidative Dehydrogenation Process

The processes disclosed herein may be used to convert gaseous hydrocarbons into olefins. In some embodiments, gaseous hydrocarbons such as ethane, propane, butane and mixtures thereof may be used. Suitably, the hydrocarbon is a paraffin-containing feed including hydrocarbons having at least two carbon atoms. In some embodiments, processes disclosed herein may be used to convert ethane to ethylene. In other embodiments, processes disclosed herein may be used to convert n-butenes to butadienes. In yet other embodiments, processes disclosed herein may be used to convert ethylbenzene to styrene. Oxidative dehydration of other paraffins and olefins may also be performed using embodiments of the processes disclosed herein.

Hydrocarbon feeds including ethane may be from any number of sources, including natural gas, provided that impurities are removed sufficiently to prevent catalyst poisons and eventual product contaminants, and also to avoid economically excessive content of other accompanying compounds, including hydrocarbons, hydrogen, carbon dioxide, etc. This can be accomplished by conventional means known to those skilled in the art.

Other ethane feed sources may include ethane byproduct from a pyrolysis plant (steam cracker, autothermal cracker) that might otherwise be recycled to the pyrolysis plant for further cracking to ethylene. Instead, this pyrolysis ethane can be fed to ethane ODH processes disclosed herein. Typically, this pyrolysis ethane is already at a very high purity and is excellent feed to ethane ODH processes disclosed herein.

The feed to the ethane ODH reactor may include fresh ethane, such as from sources mentioned above, and may also include recycle of unreacted ethane recovered from the ODH reactor effluent.

The oxygen-containing gas may include air, oxygen, and/or an air/oxygen mixture. Oxygen may be "pure oxygen" or semi-pure oxygen from an oxygen plant, e.g., air separation plant, or any other suitable source. The molar ratio of molecular oxygen to hydrocarbon (e.g., ethane) in the feed for ODH processes disclosed herein may be within the range from about 0.01:1 to about 1:1.

The oxygen-containing gas may be mixed with an inert gas such as nitrogen, helium or argon. Additional feed components such as hydrogen, carbon monoxide, carbon dioxide and steam may also be included. The content of inert components (nitrogen, etc.) in the oxygen-containing gas need not be below any specific limit. However, it may be economically advantageous that the content of inert gases be limited, such as to below that representing the use of air (3.77:1 molar ratio of inert gases relative to oxygen); below a molar ratio of inert gases to oxygen of 1:1 in some embodiments; below a molar ratio of inert gases to oxygen of 0.3:1 in other embodiments; and below a molar ratio of inert gases to oxygen of 0.1:1 in yet other embodiments. Limiting inert gas components may reduce costs associated with effluent separation systems that may be required. In some embodiments, inclusion of some amount of inert gas components may be advantageous for limiting the flammability of some effluent stream(s) that may contain residual oxygen.

Steam may be provided in sufficient quantity to act as a heat diluent, limiting reaction temperature rise, and hot spots, and to avoid formation of a flammable feed mixture.

A typical feed composition, for example, may be 15 mole % ethane, 8 mole % oxygen, and 77 mole % water (steam), neglecting contents of minor constituents, or 15 mole % ethane, 38 mole % air, and 47 mole % water (steam). Such a feed composition is suitable for operation with a conversion of about 70%; thus, the 15 mole % feed ethane may include about 10.5 mole % fresh ethane and 4.5 mole % recycle ethane. For a higher ethane conversion (e.g., 80-90%) and the same inlet oxygen concentration, the feed ethane concentration may be lower, e.g., 12 mole %, with the steam concentration correspondingly higher. In the direction of lower ethane conversion per pass, a feed composition consistent with about 60% ethane conversion may be 20 mole % ethane, 9 mole % oxygen, and 71 mole % water (steam), or 20 mole % ethane, 43 mole % air and 37 mole % water (steam). At about 50% ethane conversion per pass, the feed composition may be 30 mole % ethane, 10 mole % oxygen, and 60 mole % water (steam), or 30 mole % ethane, 48 mole % air and 22 mole % water (steam). At about 40% ethane conversion per pass, the feed composition may be 40 mole % ethane, 12 mole % oxygen, and 48 mole % water (steam), or 40 mole % ethane, 57 mole % air and 3 mole % water (steam). At about 30% ethane conversion per pass, the feed composition may be 70 mole % ethane, 15 mole % oxygen, and 15 mole % water (steam).

The concentration of oxygen in the feed may be limited with a margin below the minimum oxygen for combustion at the hydrocarbon-rich concentration of the mixture (by using sufficient steam and/or inert gas, e.g. nitrogen, and/or high enough hydrocarbon concentration) in order to have a non-flammable feed mixture, in particular when the feed hydrocarbon and oxygen are premixed prior to entering the reactor, as with the use of a fixed bed reactor. The examples of elevated feed concentration and allowable feed oxygen (or air) concentration and corresponding ethane conversion per pass disclosed above are based on a representative margin relative to the flammability diagram of ethane in oxygen and inert (nitrogen and/or steam) for a pressure and temperature level that may be used when the hydrocarbon and oxygen feed streams are pre-mixed, as when using a fixed-bed reactor system. The values are realistic but illustrative. Some alteration in the allowable feed oxygen (or air) concentration may be incorporated depending on how large a safety margin is provided relative to the flammability envelope and on what pressures and temperatures are utilized. With special mixing and feed inlet designs and safety systems, and provided that the reactor system can adequately remove the large heat of reaction, including locally intense regions ("hot spots"), it may be possible to allow even higher feed oxygen (or air) concentration than the flammable amount. This may also involve special heat removal design and/or catalyst particles.

The feed ratio of ethane to oxygen may be set appropriately to obtain the desired combination of conversions of ethane and oxygen, which are inter-related by material balances and reaction selectivities. Use of a large content of steam as diluent provides considerable advantages for its heat dilution capacity and also for reducing the flammability envelope (increasing the minimum oxygen for combustion), but increases the processing costs for steam itself. Conversely, use of an elevated concentration of ethane can allow reduction in the steam concentration, reducing the costs related to the steam but increasing costs related to ethane recycle. An extra impact of elevating the ethane concentration is that it can permit increase in the allowable oxygen concentration due to the relationship of the flammability envelope. This can allow further lowering of the required steam concentration. Considering advantages of an elevated feed ethane concentration, it can be economical to utilize a lower ethane conversion, e.g. down to 60%, to 50%, to 40%, even to 20-30%. It can be seen that, though there is a debit for increased ethane recycle, there are benefits for higher concentration of the reactants and products and correspondingly lower diluent (steam) requirement and total volumetric flow rate and equipment sizing for a given ethylene production rate. In addition, there is a substantial benefit from higher selectivity at the lower conversion level. The optimum conversion level may depend on the pricing values at a specific plant site.

The feed components, ethane, oxygen/air, water, etc., may be vaporized, preheated and mixed to the extent practical prior to feeding to the ODH reactor. This can be accomplished by means known to those skilled in the art. Preheat techniques may include, for example, heat exchange from steam, a heat transfer fluid, reactor effluent, and a furnace.

The ODH reactor may be a fixed-bed reactor with high heat removal, such as a multi-tube shell-and-tube reactor/heat exchanger with catalyst and process flow inside the tubes and a heat transfer fluid (or steam generation) circulated in the shell side.

Another example is a fixed-bed reactor with catalyst in the shell side and heat removal tubes inside the catalyst bed. Yet another example is a plate-and-frame reactor/heat exchanger, such as a DEG "Thermoplate Reactor" or a Casale "Plate Cooled" Reactor with catalyst and process flow in the channel on one side of a plate and a heat transfer fluid in the channel on the other side of the plate, having alternating plates and channels. Another example of a suitable reactor includes a micro-channel reactor/heat exchanger.

As an alternative, the ODH reactor may be a fluidized-bed reactor with high heat removal. A fluidized-bed reactor may result in greater isothermicity, avoidance of hot spots, and may also allow the feeds to be introduced separately, without pre-mixing. This can eliminate constraints on overall feed concentration related to hot spots and flammability, and allow the use of a much higher concentration of primary reactants (ethane and oxygen), with a corresponding reduction in steam (and/or nitrogen) for dilution. Various fluidized-bed reactor systems may be used, including dense bed (from gently bubbling up to turbulent bed), highly expanded bed ("fast fluid bed" or "circulating fluid bed"), entrained flow ("riser" or "downer"), or combinations. Heat removal can be to a heat transfer fluid or steam generation, through coils submerged in the bed and/or freeboard (above the bed), through the vessel wall, from a connected vessel with the catalyst particles transferred from one vessel to the other, etc. Another fluidized bed system can be a "separated red/ox" fluidized bed system, where the ethane is oxidatively dehydrogenated by the oxygen contained in the catalyst in one vessel, and the [O]-depleted catalyst is transferred to a second vessel to replenish its oxygen (plus burn off any coke that has been formed). Then the oxygen-rich catalyst is returned to the oxydehydrogenation reactor. The system also has heat removal coils.

Typically $O_2$ in the overall feed to the ODH reactor will be greater than about 3%, preferably the $O_2$ feed is greater that 6 mol %. Overall ethane in the feed to the ODH reactor should be at least about 5%, preferably greater than about 10 mol %. The ODH reactor bed temperature should be between about 250 and 450° C., preferably between about 300 and 400° C. The reactor pressure should be between 0.1 and 20 barg, preferably between 0.5 and 10 barg.

One or more of the feeds may be fed in stages; i.e., a portion at the reactor inlet, a further portion at some midpoint, etc.

This can be done to some extent with fixed-bed reactors, particularly if several catalyst stages are used (stage 1, stage 2, etc.). It is especially feasible in a fluidized-bed reactor system.

The reactor system may include a single stage or there may be several stages. The stages may be of the same type (fixed bed, fluidized bed) or can be of different types. The catalyst or its concentration (e.g., mixed with some solid diluent) or size/shape contained in each stage may be the same or different. The temperature in each reaction stage may be the same or different. As noted above, a portion of one or more feed component may be delayed to a later stage. Catalyst and heat removal may be different from one stage to the next, for example (1) a first stage with preheat, (2) a second stage, or combined with the first stage, with high activity catalyst and with minimal or no heat removal in order to facilitate final preheat taking advantage of the reaction exotherm, and possibly with less void fraction in order to ensure establishment of good flow distribution, (3) a third stage with catalyst of moderated activity, possibly diluted with inert components, etc., together with maximum heat removal design for that stage and its catalyst (possibly more void fraction), (4) a fourth stage with catalyst of maximum activity and selectivity and most suitable temperature to drive toward full conversions at peak selectivity, (5) a final stage that may serve as a "quench" stage, e.g., with lower temperature or with added water/steam. Conversely, with oxygen or air to the first reactor stage possibly limited in order to keep the oxygen feed concentration below its flammability limit and/or to avoid excessive heat generation and hot spot in the first stage(s), additional oxygen or air may be fed to a later stage in order to boost the overall production in a single reaction "train" and to minimize the overall dilution of the full process flow through the system.

The heat that is removed from the reactor and its effluent may be transferred to reactor feed heatup or to a heat transfer fluid for subsequent further heat transfer. The removed heat may also be used for steam generation (or boiler feed water preheat) for use as an energy source, including as steam itself or further transformed into power. Energy export, for example, to an adjacent air separation plant that provides the oxygen feed may be particularly synergistic.

The effluent from the reactor will typically contain ethylene, added water, if used, and additional water formed by the ODH reaction, $CO_x$ and small amounts of other impurities (from the feed and from additional reactions) in addition to residual amounts of unreacted ethane and oxygen. The effluent may also contain inert gases, especially when air is used to supply oxygen to the ODH reactor.

In some embodiments, the effluent from the ODH reactor may contain in excess of 0.1 mole % oxygen; greater than 0.2 mole % oxygen in other embodiments; greater than 0.3 mole % oxygen in other embodiments; greater than 0.5 mole % oxygen in other embodiments; greater than 1 mole % oxygen in other embodiments; greater than 2 mole % oxygen in other embodiments; greater than 3 mole % oxygen in other embodiments; greater than 4 mole % oxygen in other embodiments; and greater than 5 mole % oxygen in yet other embodiments.

At the moderate reactor and effluent conditions, it is possible to control the effluent to contain a finite optimum oxygen partial pressure rather than be essentially absent, and also impose a profile of the oxygen partial pressure from reactor inlet to outlet. This provides a benefit for the catalyst in terms of both the catalyst reactive state (ideal oxidation level) for most active and selective performance and also long-term, stable performance by preventing coking and other effects. The effluent oxygen concentration from reaction stage(s) may be important for controlling the performance (i.e., conversions and selectivities) of the ODH stage(s). The oxygen conversion is a key reaction result and may be used to set the residence times and temperatures.

In some embodiments, it may be advantageous to include an oxygen elimination reactor downstream of the ethane ODH reactor in order to reduce the effluent oxygen concentration to a lower level than achievable in the ODH reactor at either advantageous or economically practical conditions, e.g., residence time or reactor temperature, or performance results, e.g., ethane conversion or ethylene selectivity, or catalyst stability. When an oxygen elimination reactor is included downstream of the ODH reactor, it can be possible to allow even higher oxygen concentration (within a moderate range) in the ethane ODH reactor effluent and thereby obtain better conditions in the ethane ODH reactor for the catalyst quantity (less catalyst and residence time since lower oxygen conversion is required), performance, stability and life, and overall optimum ethane conversion and ethylene selectivity and yield as well. Processes useful for removal of oxygen from hydrocarbon streams may include those disclosed in U.S. Pat. Nos. 4,299,800, 5,157,204, and 6,747,066, among others, for example. Catalysts useful in an oxygen elimination reactor may include oxygenation catalysts, combustion catalysts, and hydrogenation catalysts, among others.

The ethane ODH reactor effluent oxygen concentration may be in the range of 0.1-5 mole % in some embodiments. The inclusion of an oxygen elimination reactor is especially advantageous for ethane ODH reactor effluent oxygen concentrations above 0.5 mole %, but it may be used when the reactor effluent oxygen concentration is lower as well.

One type of oxygen elimination reactor uses an oxidation catalyst to have the oxygen in the ethane ODH reactor effluent combust CO plus a portion of the ethylene and unconverted ethane. The combustion of the $C_2$s represents yield loss, but is not excessive when the ethane ODH reactor effluent oxygen concentration is not higher than 1-2 mole %, considering that the consumption of ethane and ethylene during complete combustion to $CO_2$ and $H_2O$ is only 0.29 and 0.33 moles/mole oxygen consumed, respectively. The catalyst, conditions, and conversions cited in U.S. Pat. No. 5,446,232 are illustrative of an appropriate system. This includes a reactor temperature of 200-300° C., thus equal to or cooler than the ethane ODH reactor. Cooling the ethane ODH reactor effluent prior to the oxygen elimination reactor is highly appropriate and compatible. Of course, it is preferred for the oxygen elimination reactor to obtain complete combustion of CO and whatever amount of $C_2$s to $CO_2$ and $H_2O$ rather than to CO, partially oxygenated hydrocarbon by-products, and $H_2$. This is to minimize consumption of the $C_2$s in their partial or full combustion reactions and also to minimize the CO in the final effluent.

Like the ethane ODH reactor, the oxygen elimination reactor may be any of various types of reactors (fixed bed, fluid bed). It is preferable that it also have high heat removal capability, as the heat release can otherwise produce a large temperature rise, especially if the inlet oxygen concentration is higher than 0.5 mole %. On the other hand, since the inlet oxygen concentration is much lower than the overall inlet to the ethane ODH reactor, flammability is no longer an issue and the advantage of a fluidized bed is not as strong for the oxygen elimination reactor from that perspective as for the ethane ODH reactor.

The oxygen elimination reactor may be in a separate vessel from the ethane ODH reactor, or a possible embodiment is for it to be in the same vessel, e.g., as a final "stage" (especially if it uses the same type reactor). An advantage of using separate vessels is the ability to handle the oxygen elimination catalyst differently from the ethane ODH catalyst, e.g., if there is a need for more frequent regenerations or replacements. Additionally, in some embodiments, there may be more than one oxygen elimination reactor in parallel, allowing catalyst in one to be changed while the other is on-line, without shutting down the ethane ODH reactor.

An option for the oxygen elimination reactor is to add a combustible to the oxygen elimination reactor feed, e.g., $H_2$ or a hydrocarbon, in order to both [a] facilitate the combustion consumption of the oxygen and [b] consume the added combustible instead of the more valuable ethylene or residual ethane, especially to the extent that the oxygen elimination catalyst and conditions can obtain selective combustion of CO and the added combustible relative to the $C_2$s.

Another type of oxygen elimination reactor is for it to be a final ethane ODH stage with significantly different conditions from the main ethane ODH stage(s) in these embodiments, operated to drive the oxygen to elimination, while still producing more ethylene by ODH. Such different operation may be with the same or different catalyst and may be in the same vessel or one or more separate vessel(s), as described above for the first type of oxygen elimination reactor.

Another option is to use both a final ethane ODH stage with its emphasis on driving the oxygen toward elimination while obtaining additional product ethylene followed by an oxygen elimination reactor using combustion. Again, these stages or reactors may be in separate vessels or some stages/reactors combined into a common vessel.

Yet another type of oxygen elimination reactor may incorporate addition of $H_2$ and a hydrogenation catalyst to hydrogenate the oxygen (rather than oxidation catalyst to accomplish combustion). Such a system may have additional benefit of hydrogenating various by-products to the extent that some may be present, such as acetylene and oxygenates.

As with the ODH reactor, the heat that is removed from the oxygen elimination reactor and its effluent may be transferred to ODH reactor feed heatup or to a heat transfer fluid for subsequent further heat transfer. The removed heat may also be used for steam generation (or boiler feed water preheat) for use as an energy source, including as steam itself or further transformed into power.

The effluent from the ethane ODH reactor, and thereafter from the oxygen elimination reactor, if used, will have a high content of $H_2O$, particularly for operation at high ODH conversion if a fixed-bed reactor system is utilized (operation at low ODH conversion with high ethane recycle and feed concentration, or highly concentrated with a fluidized bed reactor system, can have a much lower $H_2O$ concentration). The effluent may be cooled and much of its water content condensed prior to compressing the gases. The condensed water may be recycled to provide steam dilution of the reactor feed. Net water generated by reaction is purged from the system. Energy recovery from the condensing water may be accomplished by means known to those skilled in the art.

The condensation of the large amount of effluent water greatly reduces the flow rate of the remaining vapor phase and correspondingly results in a large increase in the concentration of the non-condensing components. This may result in a decrease in the cost of the subsequent processing. However, it is important to recognize that any oxygen that might be present (especially if there is no oxygen elimination reactor prior to water condensation, or to the extent that the oxygen elimination is less than 100% complete) will become much higher than before the water condensation. This concentrating effect on the non-condensing vapor will increase further with successive processing, i.e., compression and further water knock-out, removal of $CO_2$, and eventually condensation of hydrocarbons (ethane, ethylene, and any other $C_{2+}$ hydrocarbons) in the recovery system. A seemingly low concentration of oxygen in the effluent from the ethane ODH reactor (or subsequent to any oxygen elimination reactor) can become a high and possibly flammable concentration in downstream processing. This has important impacts for the design and operation of the recovery system, and is a reason that it is important to accomplish the oxygen elimination to a high level prior to the steps that condense and remove the condensable components.

If the oxygen elimination has been less than 100%, it may be appropriate to add an oxygen adsorber for final removal prior to the condensation of hydrocarbons. An alternative approach may be to accept the presence of a small residual amount of oxygen in the stream and add some gaseous diluent (e.g., nitrogen or methane) at that point to avoid emergence of a gas stream which is self-flammable (inside the flammability envelope without requiring additional oxygen or combustible). If methane is used, the final off-gas may be utilized as a fuel gas. If nitrogen is used, the nitrogen might be obtained from the same air separation plant that provides the oxygen for the ethane ODH reactor. If air has been used in the ODH reactor, the residual nitrogen may already provide sufficient dilution of the final off-gas. Even if the oxygen-containing gas for the ODH reactor is oxygen from an air separation plant, it may contain a sufficient content of inert gas compounds to provide adequate dilution of the final off-gas, either as supplied from the air separation plant or by use of lower oxygen purity or by mixing with a moderate amount of air prior to feeding to the ODH reactor.

It has been mentioned above that the oxygen elimination reactor may accomplish some additional goals related to eliminating undesirable byproducts, such as CO, acetylene, and oxygenates. Nevertheless, it may still be advantageous or necessary to incorporate appropriate processing steps at and downstream of the water condensation and compression for the processing, including ultimate removal of these byproducts by means known to those skilled in the art.

Following oxygen elimination, water separation, carbon dioxide recovery, and nitrogen separation, each where required, the ethylene product may be separated from the residual ethane, any heavy byproducts, light byproducts and residual gases, plus impurities that boil close to the product ethylene and the ethane that is recycled, by means known to those skilled in the art. In addition, as a benefit of limiting the amount of the compounds other than ethylene and ethane generated using processes and catalysts disclosed herein, the separations may be accomplished with less investment and operating cost than for conventional steam cracking of ethane.

The major compounds whose processing and separation have greatest impact on the cost are the unconverted ethane for recycle and the dilution water, also for recycle, both of which are dependent on the conversion per pass that is utilized and the corresponding appropriate feed composition. The ethane recycle rate and its cost impact is at its largest for operation at low ethane conversion per pass, while the steam rate and its cost impact is at its largest at the opposite condition when the ethane feed concentration is low, thus at high ethane conversion per pass, in conjunction with a fixed-bed ethane ODH system. The steam rate and its cost impact can be reduced if a fluidized-bed ethane ODH reactor system is used because the feeds do not have to be pre-mixed and it can therefore be possible to utilize a highly concentrated overall feed composition that might even be flammable if pre-mixed. The strongest benefit in such a situation can be at high ethane conversion per pass (which also has minimal ethane recycle rate and cost). A separated red/ox fluidized bed system can even utilize air and keep its nitrogen separated from the main process flow. On the other hand, for a fixed-bed reactor system requiring avoidance of flammability when the feeds are pre-mixed, or other system utilizing feed pre-mix, an additional benefit at high ethane feed concentration (and low ethane conversion per pass) is that such a condition on the rich side of the flammability envelope allows higher oxygen concentration without becoming flammable. This permits a higher concentration of reactor feeds and products, with correspondingly lower volumetric flowrate and higher reactor productivity for additional cost benefits, together with lower steam dilution requirement, while also obtaining heightened selectivity.

Nitrogen also has a major impact on effluent processing, separations and costs, if it is a major component of the feed, as when air is utilized for the oxygen supply (unless it is kept separate by use of a separated red/ox fluidized bed system). On the beneficial side, when present, nitrogen is an additional inert with respect to how concentrated the reaction mixture is and how close to flammability it is, and also effluent and offgas streams as discussed above, etc. Nitrogen, steam and high ethane concentration are alternative compounds with major cost impact each of which can be considered and compared for an economical process, including use of a combination.

The ODH catalysts described herein enable the use of much less severe and sensitive conditions than used in the thermal cracking and autothermal cracking processes, and also in previous ODH development attempts. The temperatures utilized are within the ideal range from about 200° C. to about 500° C., preferably from about 300° C. to about 450° C. (relatively mild, but still hot enough for excellent, efficient recovery of the large exothermic reaction heat release); the superficial residence times are in the practical range of 0.1-10 seconds, preferably 0.5-5 seconds, without a critical need of quick quenching; and the pressure is in the moderate range of about 0.1-30 barG, preferably 0.1 to 20 barG. The reaction is exothermic, such that temperature control is by conventional heat removal at the temperature range mentioned, with convenient transfer to inexpensive steam cogeneration, with side benefit of its energy for heat and/or power utilization. With the moderate conditions (and the catalyst characteristics), the catalyzed ODH reaction may be accomplished with essential avoidance of multiple side reactions.

Equipment that may be used in the process described above includes conventional reactors, etc., at moderate conditions. They are amenable and economical for use in process plants that can be either large or small, unlike standard steam cracking whose complex furnace reactors are economical only when built for very large plants.

The ODH effluent resulting from processes disclosed herein typically requires separate processing through some initial steps, but may also be integrated with pyrolysis plant product gas separation and purification systems in downstream steps. This approach may be economically preferred when incorporated into the original design of a pyrolysis plant with further conversion of its pyrolysis ethane to additional ethylene, due to both higher overall selectivity/production of ethylene and lower investment, than when a pyrolysis ethane recycle cracker is utilized. Processes disclosed herein may also be used to retrofit an existing pyrolysis plant and release capacity of existing recycle ethane cracking furnace(s) and possibly their portion of the existing compression train for those to be used for increasing the feed rate of the pyrolysis plant and overall ethylene production for the retrofitted plant.

Referring now to FIGS. 1-4, various ODH processes according to embodiments disclosed herein are illustrated, where like numerals represent like parts.

Referring now to FIG. 1, hydrocarbon stream 6, including fresh hydrocarbon 2 and recycle hydrocarbon 4, if used, may be fed to oxidative dehydrogenation reactor 12, which includes oxidative dehydrogenation catalysts as disclosed herein, such as in a packed or fluidized bed, or a separated red/ox fluidized bed system. An oxygen-containing gas 8, such as air, and dilution steam 10 may also be fed to oxidative dehydrogenation reactor 12. Contact of the hydrocarbon and oxygen in the presence of the catalyst at appropriate reaction conditions, as described above, converts at least a portion of the hydrocarbons to olefins, water, and reaction byproducts, if any. The reactor effluent, which may include unreacted oxygen, unreacted hydrocarbons and nitrogen as well as the olefins, water and reaction byproducts, may be recovered via flow stream 14.

If necessary or desired, the reactor effluent may then be fed via flow stream 14 to an oxygen elimination reactor 18, providing for consumption of part or all of the remaining oxygen by combustion reactions. Additionally, added combustible, such as hydrogen or hydrocarbons such as methane, propane or other, may be added via flow line 16 to be combusted preferentially instead of the olefin product and feed hydrocarbons.

Effluent from the oxygen elimination reactor, or directly from the ODH reactor, may be recovered via flow line 20 and fed to quench unit 22 to reduce the effluent temperature and also condense and separate a large portion of the water content, in advance of downstream processing. Water may be recovered from quench unit 22 via flow line 24, at least a portion of which may be recycled to oxidative dehydrogenation reactor 12 via flow line 10. Water not recycled may be withdrawn from the system via flow line 26, representing most of the water generated in the ODH and oxygen elimination reactors.

The hydrocarbons, dilution gases such as nitrogen, if present, and byproduct gases such as carbon oxides and acetylene, may then be fed via flow line 28 to compression unit 30, where compression of the gases may result in removal of additional water recovered via flow line 32. The resulting compressed stream 34 may then be processed to separate carbon dioxide from the hydrocarbons in $CO_2$ removal unit 36. The $CO_2$ is withdrawn in flow line 38, which may include additional compounds associated with its removal. The remaining components, including unreacted hydrocarbons, olefins, light and heavy byproducts, diluent gases, and any residual amount of water, may then be fed via flow line 40 through dryer 42.

The dried stream 44 is sent to gas separation unit 46, which removes the offgas that contains any inert gas, residual oxygen, carbon monoxide, methane if present, and other non-condensables. The $C_2+$ compounds leave in flow stream 50. Prior to its discharge, offgas flow stream 48 may have processing step(s) to recover $C_{2+}$ so that it can join flow stream 50. This is especially true the more nitrogen or other inert gases have been fed into the process (e.g., in air as the oxygen source) and ends up in offgas flow stream 48.

The $C_{2+}$ compounds are fed via flow line 50 to the hydrocarbon separation and purification system 52, where the product ethylene stream 56 is separated, purified and delivered. Other hydrocarbon streams that are separated may include stream 54 with compounds that are lighter than the product ethylene, unreacted feed ethane 58, and compounds heavier than ethane 60. Stream 54 may be recycled to distribute its lighter compounds to the offgas stream 48 and recover its ethylene, eventually to product stream 56. At least a portion of the recovered unreacted ethane 58 may be recycled to oxidative dehydrogenation reactor 12 via recycle line 4, as mentioned above. The heavy compounds 60 may be discharged for further use.

The fresh ethane feed stream 2 may be pre-fractionated in order to remove its lighter and/or heavier compounds prior to being fed to the ODH reactor. This pre-fractionation fractionation may be accomplished in conjunction with the effluent hydrocarbon separation and purification system 52.

The $CO_2$ removal unit 36 and drier 42 may be positioned at a later point in the hydrocarbon separation and purification system 52. There may also be hydrogenation of acetylene and possibly other acetylenic compounds. All of the processing may be in accordance with approaches and conditions known to those skilled in the art, but incorporating alterations and savings due to greatly lowered contents of byproducts other than $CO_x$ and water.

Figure 2:
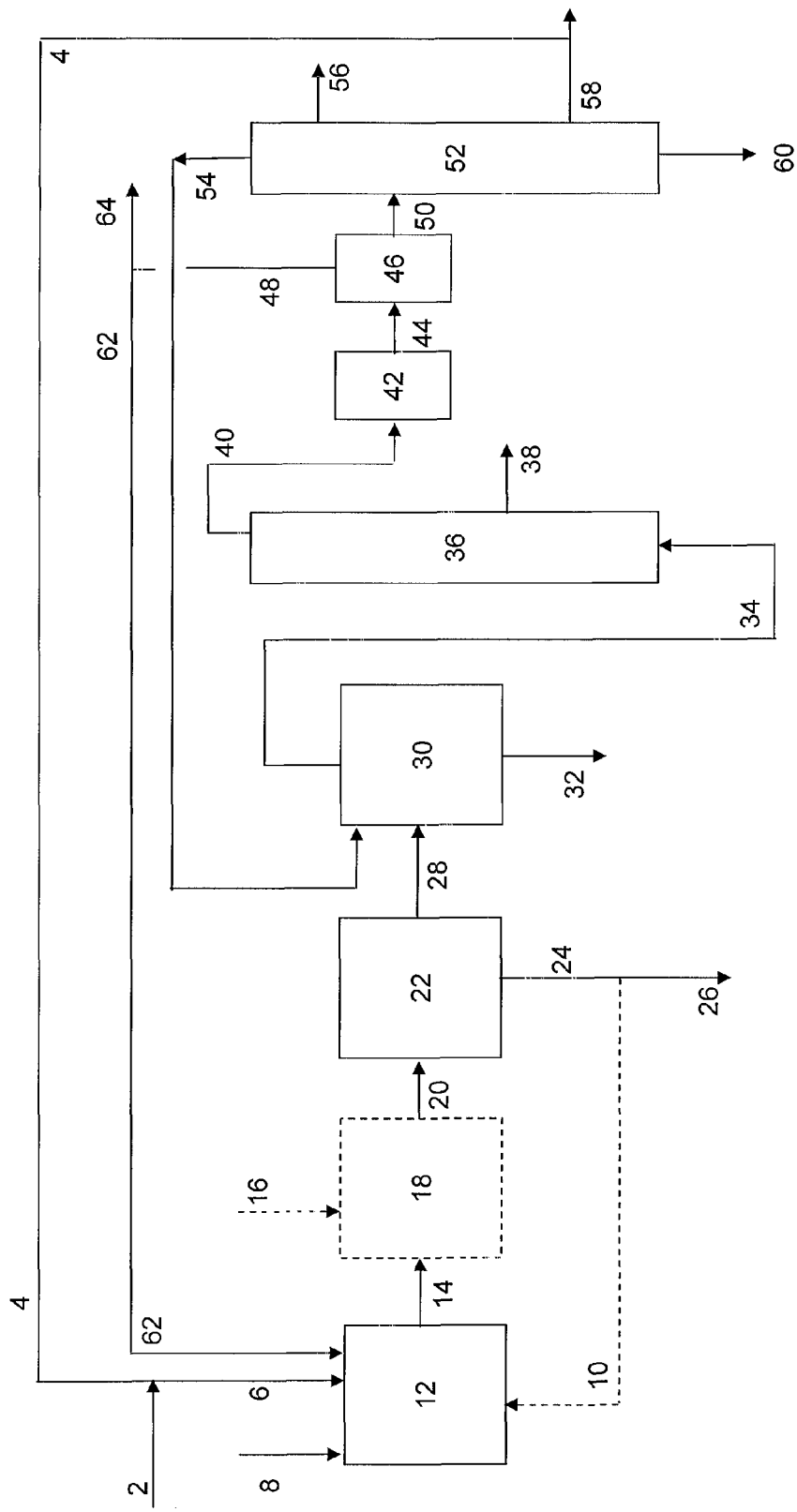
FIG. 2 is a simplified process flow diagram for oxidative dehydrogenation processes according to embodiments disclosed herein.

In the embodiment illustrated in FIG. 2, in lieu of recycling some portion of the water from quench unit 22, at least a portion of the nitrogen recovered via gas separation unit 46 may be recycled via flow line 62 as dilution gas to oxidative dehydrogenation reactor 12. Net offgas is purged via flow stream 64.

Figure 3:
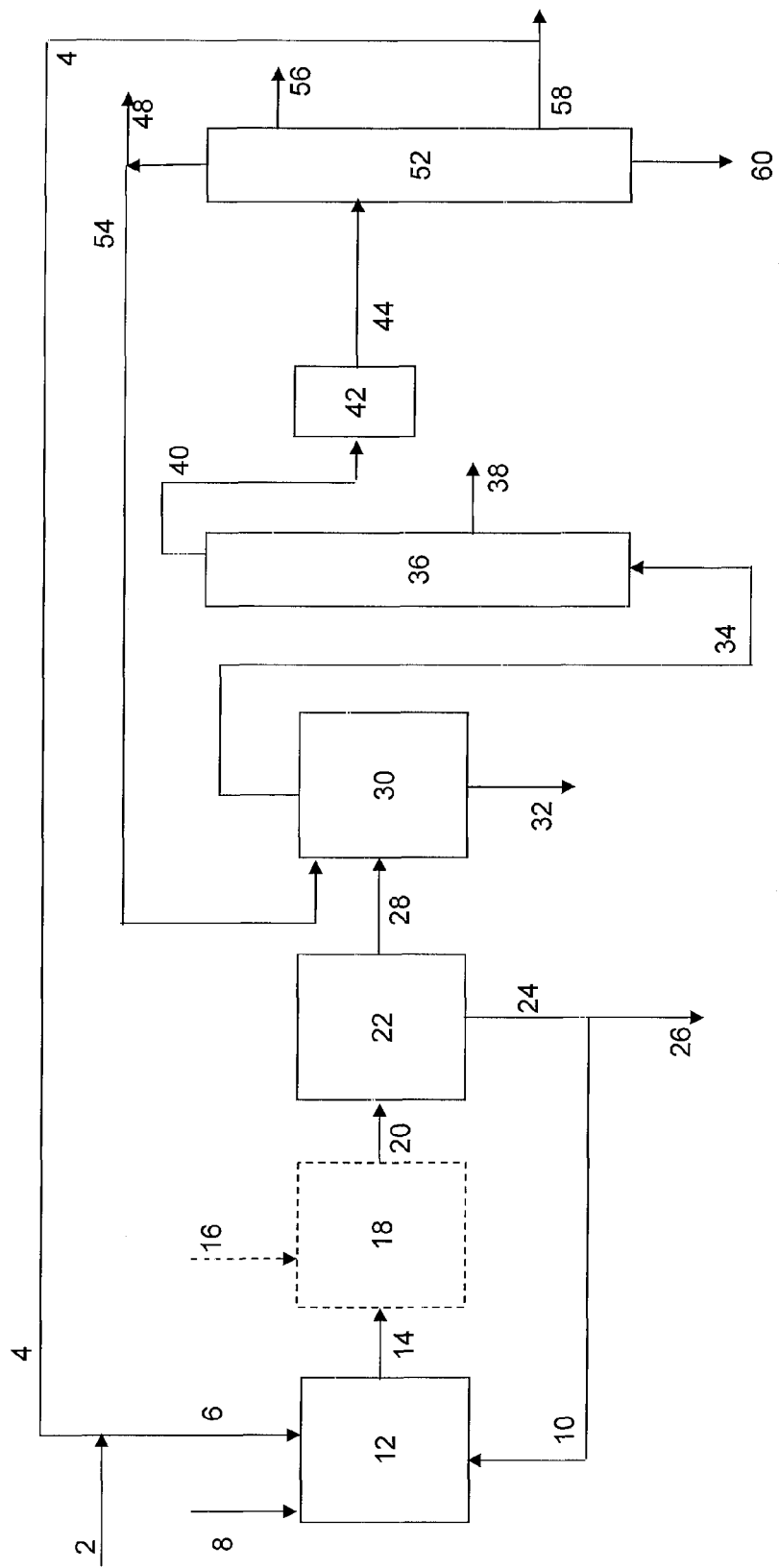
FIG. 3 is a simplified process flow diagram for oxidative dehydrogenation processes according to embodiments disclosed herein.

In the embodiment illustrated in FIG. 3, oxygen-containing gas stream 8 may contain higher oxygen concentration (lower content of inert gases) than in air. As a result, it may be possible to simplify separation and purification systems 46 and 52 due to much lower content of inert gases. FIG. 3 depicts the gas separation to be incorporated modestly into the hydrocarbon separation and purification system 52, with offgas purge 48. Various options exist for recovering $C_2+$ from the offgas plus light hydrocarbons.

Figure 4:
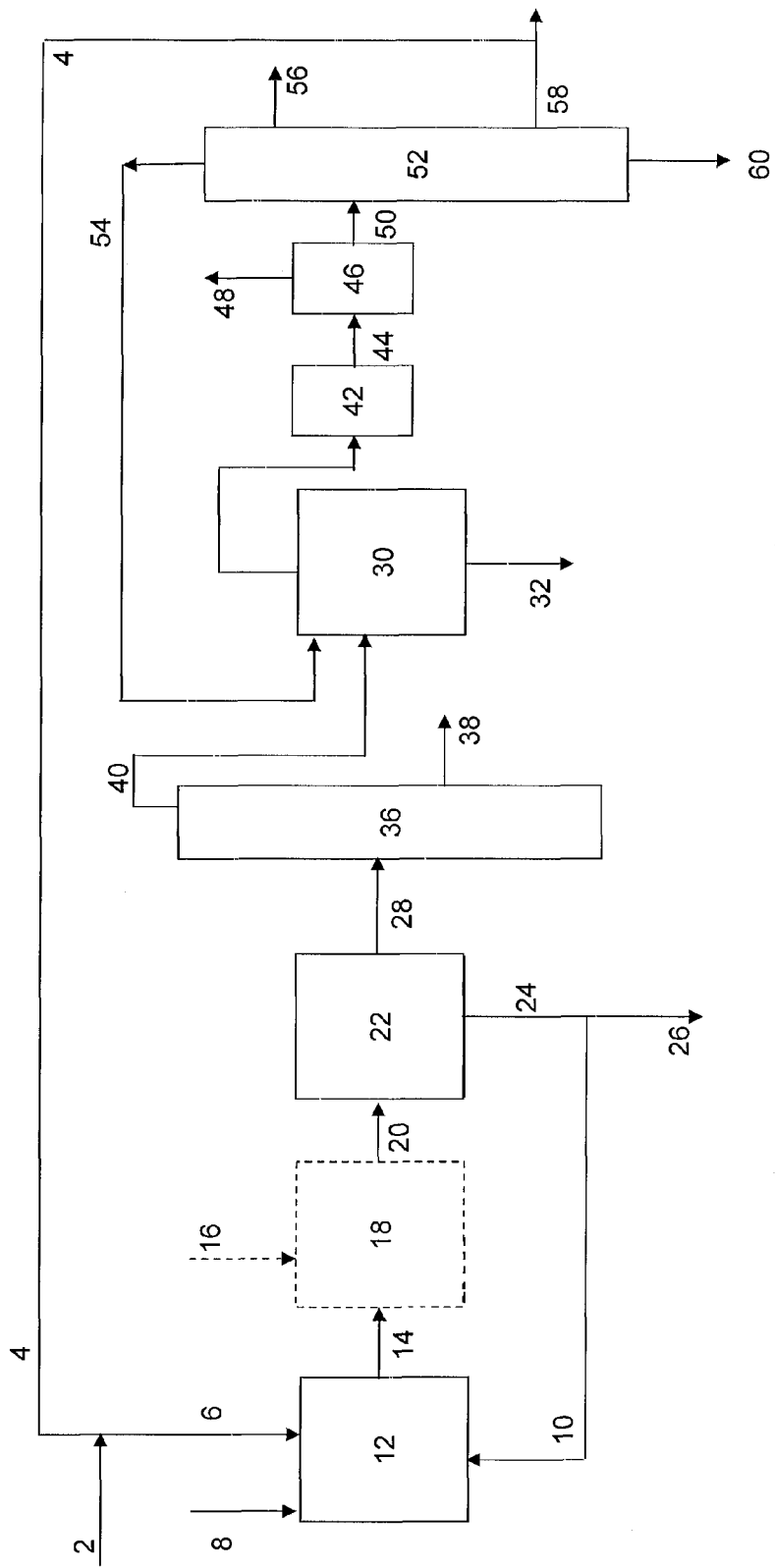
FIG. 4 is a simplified process flow diagram for oxidative dehydrogenation processes according to embodiments disclosed herein.

In the embodiment illustrated in FIG. 4, carbon dioxide present in stream 28 following quench unit 22, may be separated in $CO_2$ removal unit 36 prior to compressing the main effluent gases in unit 30, as an alternative option rather than removing the $CO_2$ after compression. Carbon dioxide may be recovered via flow stream 38, and stream 40 with the hydrocarbons, including ethane and ethylene, may then be compressed 30, dried 42, and separated between offgas and $C_2+$hydrocarbons via gas separation unit 46. The $C_{2+}$ hydrocarbon mixture, including ethane/ethylene, may then be separated and purified in system 52 as discussed above.

Several positions for $CO_2$ removal have been illustrated in FIGS. 1 and 4 and in the discussion above. Other possible positions include together with (aqueous system), or upstream of (dry, hot system), the water quench unit 22 prior to compression, as described. $CO_2$ removal depends on whether it has high concentration and thus sufficient partial pressure. In addition, as also applies to other processing steps, two or more steps may be incorporated for optimum processing, including also the possibility of the first stage upstream of some other processing step (e.g., compression) and the second stage downstream.

Other useful flow schemes are contemplated via embodiments disclosed herein.

EXAMPLES

Testing Procedures

Evaluation of catalysts for ethane oxydedrogenation (ODH) is carried out in a fixed bed flow reactor. The feed compositions are various combinations of $C_2H_6/O_2/H_2O/N_2$, including molar ratios of: 10/10/10/70 (Feed A) and 15/10/10/65 (Feed B). A superficial space velocity of 1200 $h^{-1}$ is used, calculated based on volumetric flow rate of the reaction mixture at standard conditions of 1 atmosphere and 25° C., together with the reactor volume occupied by the catalyst. The reactor consists of 1.0 cm (0.4 inch) ID, stainless steel tube heated in an upright Lindberg furnace and at temperatures between 250 and 500° C. In this test the reactor contains 2.5 cc of the test catalyst of 12-20 mesh size. The reactor bed depth is approximately 3.0 cm (1.2 inches). In the test with extrudates, the particle size is 1.6 mm diameter×2.0 mm length, and, again, 2.5 cc of the particles are charged. All products are analyzed through an online GC system (Perkin Elmer CLARUS 500). The GC is equipped with two detectors, TCD and FID for two separate channels. One channel with the TCD is used to analyze $H_2$, $O_2$, CO, $CO_2$, and light hydrocarbons and the other channel with FID detector is used to analyze oxygenates and long-chain or aromatic hydrocarbons.

Catalyst Preparation

Comparative Example 1

A catalyst with a nominal composition $Mo_{1.0}V_{0.43}Nb_{0.11}Sb_{0.07}Ca_{0.03}O_x$ is prepared in accordance with composition and preparation as disclosed in Example 1 of U.S. Pat. No. 4,524,236. 9.97 g of ammonium metavanadate is added to 100 mL of water and heated to 70° C. with stirring for fifteen minutes to form a solution (solution 1). Ammonium niobate (V) oxalate hydrate (20 wt % Nb content) amounting to 10.56 g, antimony (III) oxalate amounting to 3.29 g and calcium nitrate tetrahydrate amounting to 1.77 g are added to a second 100 mL of water and heated to 70° C. with stirring for fifteen minutes and a slurry is obtained. This slurry is combined with solution 1 to form second slurry and the resulting slurry is heated at 70° C. with stirring for fifteen minutes. To a third 100 mL of water is added 35.3 g of ammonium heptamolybdate tetrahydrate and the mixture is heated to 70° C. with stirring to form a solution (solution 2) and this solution is added to the above slurry to form final mixture. The final mixture is also heated at 70° C. for fifteen minutes with stirring. The water is removed from the final mixture on a rotavapor at 50° C. to obtain a solid. The solid is further dried in an oven at 120° C. overnight and then oven calcined in air at a temperature of 350° C. for five hours. The X-ray diffractogram (XRD) of the calcined material mainly shows amorphous phase. The calcined material is ground with a mortar/pestle to powder which is then pressed and sized to 12-20 mesh granules for reactor evaluation. The catalyst is tested according to the above described test procedure and results are shown in Table 1.

Comparative Example 2

A catalyst with a nominal composition $Mo_{1.0}Vo_{0.43}Nb_{0.11}Sb_{0.07}Te_{0.03}O_x$ is prepared in accordance to Example 1 of U.S. Pat. No. 4,524,236 with Ca replaced by Te. The preparation procedure is the same as described for Comparative Example 1 except that 1.40 g of telluric acid is added in place of the calcium nitrate tetrahydrate.

Comparative Example 3

Low Temperature Calcinations

Figure 5:
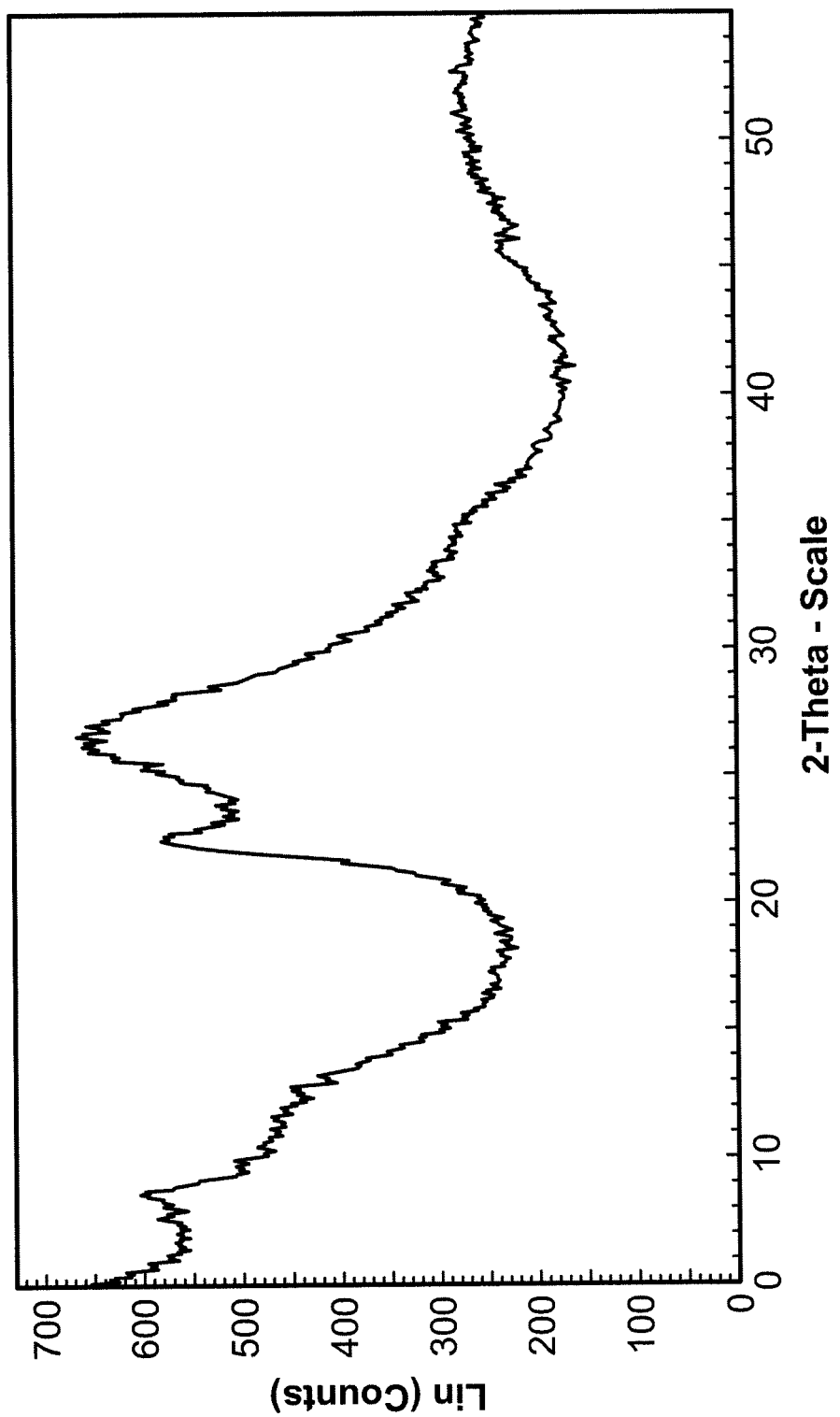
FIG. 5 is an X-ray diffractogram of a prior art catalyst.

A catalyst with a nominal composition $Mo_{1.0}V_{0.29}Nb_{0.17}Te_{0.21}Sb_{0.01}O_x$ is prepared using a different preparation procedure from Example 1 of U.S. Pat. No. 4,524,236 except for the calcination conditions. In a beaker 15.80 g of ammonium niobate (V) oxalate hydrate (20 wt % Nb content), 0.5 g of antimony oxalate and 4.0 g of oxalic acid dihydrate are dissolved in 160 mL of DI water at room temperature and a homogeneous solution (solution 1) is obtained. In a round bottom flask, 35.60 g of ammonium heptamolybdate tetrahydrate, 6.72 g of ammonium metavanadate, 9.56 g of telluric acid are dissolved in 200 mL water at 70° C. to form a second solution (solution 2). 5.0 mL of concentrated nitric acid is added to solution 2 and the resulting acidified solution is then combined with solution 1, obtaining an orange-colored gel. The water is removed from the gel on a rotavapor at 50° C. to obtain a solid. The solid is further dried in an oven at 120° C. overnight and a portion of the dried solid is calcined five hours in air at 350° C. The other portion of the dried solid is used in Example 1 for high temperature calcinations. The X-ray diffractogram (XRD) of the calcined solid mainly shows amorphous phase as illustrated in FIG. 5. The calcined material is ground with a mortar/pestle to powder which is then pressed and sized to 10-20 mesh granules for reactor evaluation.

Comparative Example 4

High Temperature Calcination in the Absence of $HNO_3$

A catalyst with a nominal composition $Mo_{1.0}V_{0.29}Nb_{0.17}Te_{0.21}Sb_{0.01}O_x$ is prepared in the absence of nitric acid in the following manner: In a beaker 7.90 g of ammonium niobate (V) oxalate hydrate (20 wt % Nb content), 0.25 g of antimony oxalate and 2.0 g of oxalic acid dihydrate are dissolved in 80 mL of DI water at room temperature and a homogeneous solution (solution 1) is obtained. In a round bottom flask, 17.84 g of ammonium heptamolybdate tetrahydrate, 3.36 g of ammonium metavanadate, 4.78 g of telluric acid are dissolved in 100 ml water at 70° C., obtaining a second solution (solution 2). Solution 2 is combined with solution 1 and an orange-colored gel is formed. The water is removed from the gel on a rotavapor at 50° C. to obtain a solid. The solid is further dried in an oven at 120° C. overnight and then calcined two hours in air at 275° C. followed by two hour calcinations at 600° C. in flowing nitrogen. The calcined material is ground with a mortar/pestle to powder which is then pressed and sized to 12-20 mesh granules for reactor evaluation.

Example 1

High Temperature Calcination in the Presence of $HNO_3$

Figure 6:
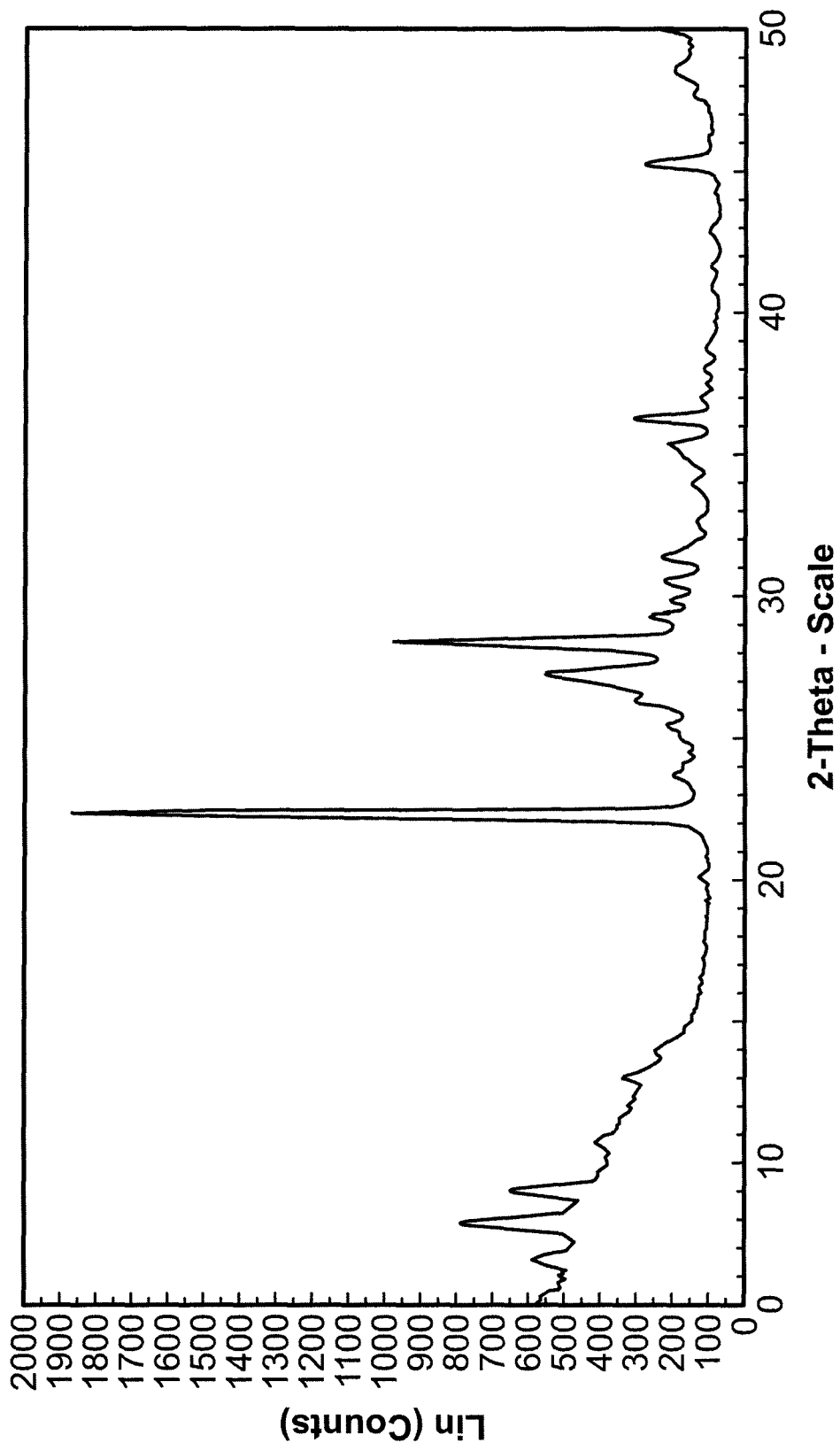
FIG. 6 is an X-ray diffractogram of a catalyst according to embodiments disclosed herein.

The portion of dried and uncalcined solid from Comparative Example 3 is first calcined two hours in air at 275° C. in an oven and then calcined two hours at 600° C. in flowing nitrogen. X-ray diffraction (XRD) of the calcined material shows the presence of two distinguished crystalline phases (hexagonal and orthorhombic phases) as illustrated in FIG. 6. The solid is ground with a mortar/pestle to powder and a portion of the powder is then pressed and sized to 12-20 mesh granules for reactor evaluation. The other portion of the powder is used for acid treatment as described in Example 3.

Example 2

The catalyst of Example 1 is tested with different feed composition as shown in Table 1.

Example 3

Figure 7:
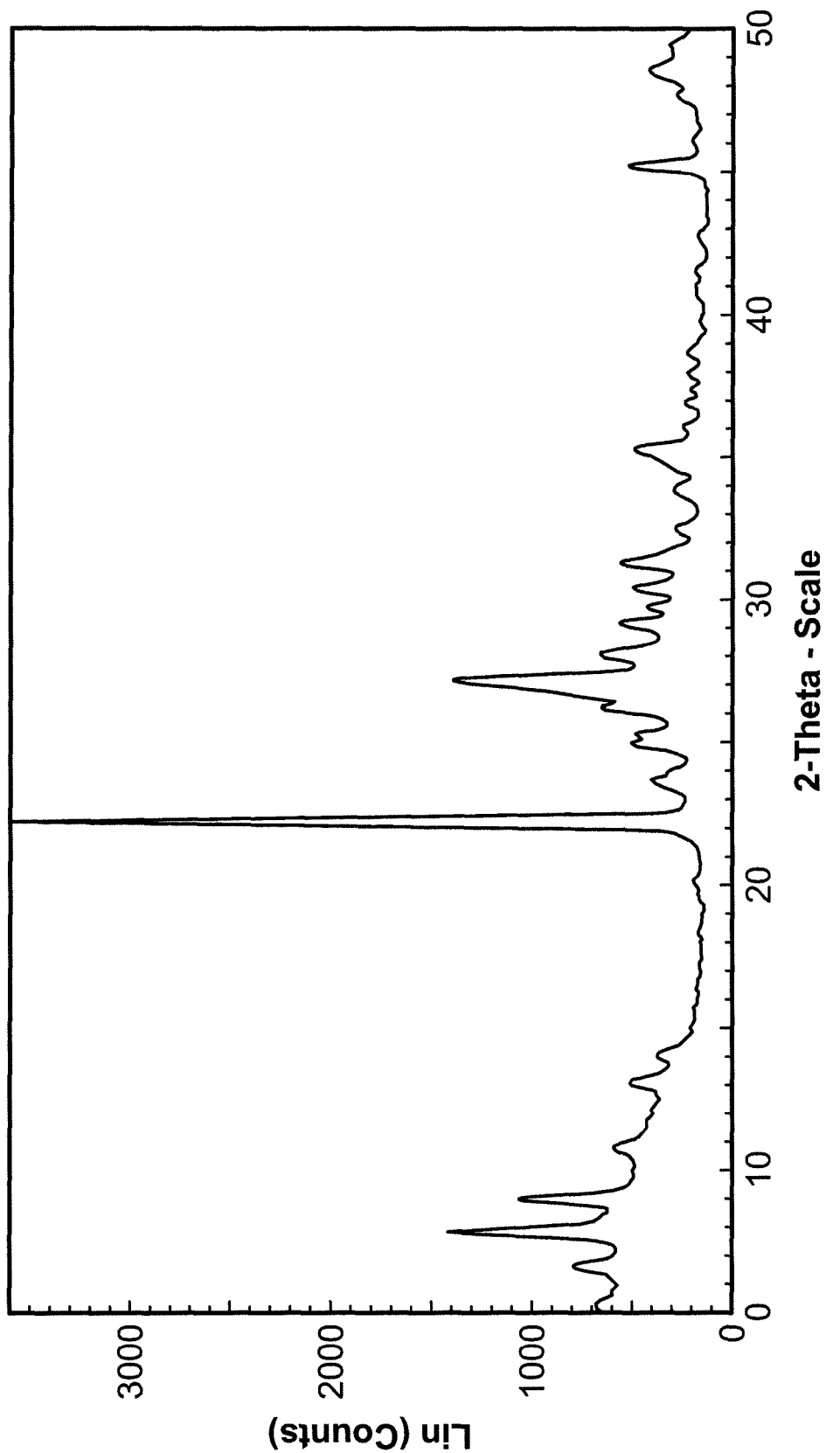
FIG. 7 is an X-ray diffractogram of a catalyst according to embodiments disclosed herein.

In a round bottom flask, 10 g of the powder of Example 1 are mixed with 10 g of oxalic acid dihydrate and 90 g of DI water. The resulting mixture is heated at 80° C. for five hours with stirring and then the solids is collected by vacuum filtration and dried in an oven at 120° C. overnight. The dried solid is heated two hours at 500° C. in flowing nitrogen. The X-ray diffractogram (XRD) of the acid-treated catalyst shows the presence of mainly one crystalline phase (orthorhombic phase) as illustrated in FIG. 7. The acid-treated catalyst is then pressed and sized to 12-20 mesh for reactor evaluation.

Example 4

High Sb

A catalyst with a nominal composition $Mo_{1.0}V_{0.29}Nb_{0.17}Te_{0.21}Sb_{0.07}O_x$ is prepared in the following: In a beaker, 7.90 g of ammonium niobate (V) oxalate hydrate (20 wt % Nb content), 1.70 g of antimony oxalate and 2.0 g of oxalic acid dihydrate are mixed with 80 mL of DI water at room temperature and slurry is obtained. In a round bottom flask, 17.84 g of ammonium heptamolybdate tetrahydrate, 3.36 g of ammonium metavanadate, 4.87 g of telluric acid are dissolved in 100 mL water at 70° C. and a homogeneous solution is obtained. 2.5 mL of concentrated nitric acid is added to the solution and the resulting acidified solution is then combined with the slurry and an orange-colored gel is formed. The water is removed from the gel on a rotavapor at 50° C. and a solid is obtained. The solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

Example 5

Low Te, 0.125 Level

A catalyst with a nominal composition $Mo_{1.0}V_{0.29}Nb_{0.17}Sb_{0.01}Te_{0.125}O_x$ is prepared in the following: In a beaker, 7.90 g of ammonium niobate (V) oxalate hydrate (20 wt % Nb content), 0.25 g of antimony oxalate and 2.0 g of oxalic acid dihydrate are mixed with 80 mL of DI water at room temperature and homogeneous solution (solution 1) is obtained. In a round bottom flask, 17.83 g of ammonium heptamolybdate tetrahydrate, 3.43 g of ammonium metavanadate and 2.90 g of telluric acid are dissolved in 100 mL water at 70° C. and a homogeneous solution (solution 2) is obtained. 2.5 mL of concentrated nitric acid is added to solution 2 and the resulting acidified solution is then combined with solution 1 and an orange-colored gel is formed. The water is removed from the gel on a rotavapor at 50° C. and a solid is obtained. This solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

Example 6

Low Te, 0.15 Level

A catalyst with a nominal composition $Mo_{1.0}V_{0.29}Nb_{0.17}Sb_{0.01}Te_{0.15}O_x$ is prepared following the same procedure as for Example 5 except that the amount of telluric acid is increased from 2.90 g to 3.41 g.

Example 7

Ni in Place of Sb

A catalyst with nominal composition $Mo_{1.0}V_{0.29}Nb_{0.17}Te_{0.10}Ni_{0.04}O_x$ is prepared in the following manner: In a beaker, 7.90 g of niobium oxalate and 2.0 g of oxalic acid dihydrate are dissolved in 80 mL DI water (solution 1) at room temperature and a homogeneous solution (solution 1) is formed. In a round bottom flask, 17.84 g of ammonium heptamolybdate tetrahydrate, 3.36 g of ammonium metavanadate, 2.32 g of telluric acid and 1.21 g of nickel nitrate hexahydrate are dissolved in 100 mL of DI water at 70° C. (solution 2). 2.5 mL of concentrated nitric acid is added to solution 2 and then combined with solution 1 to form a gel. The water is removed from the gel on a rotavapor at 50° C., obtaining a solid. The solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

C. followed by two hour calcination at 600° C. in flowing nitrogen. A portion of the calcined solid is pressed and sized to 12-20 mesh for reactor evaluation. The test results and BET surface area are shown in Table 2.

Example 8

Analytical Grinder 10 g of the calcined solid of Comparative Example 5 are ground with a Tekmar A-10 Analytical Mill: two minutes for every five grams. BET analysis of the ground powder shows 8.2 m²/g surface area. The powder is pressed and sized to 12-20 mesh for reactor evaluation.

Example 9

Cryogenic Grinding, 2 min 50 g of the calcined solid of Comparative Example 5 are ground with a Freezer Mill (model #6770, Spex): two minutes for every five grams. BET analysis of the ground powder

TABLE 1

| Example | Catalyst | Feed | Test Condition Temp (° C.) | Performance $C_2$ % Conv | $C_2^=$ C % Sel | $C_2^=$ C % Yield |
|---|---|---|---|---|---|---|
| Comp. Ex. 1 | $Mo_{1.0}V_{0.43}Nb_{0.11}Sb_{0.07}Ca_{0.03}O_x$ | A | 400 | 67 | 62 | 42 |
| Comp. Ex. 2 | $Mo_{1.0}V_{0.43}Nb_{0.11}Sb_{0.07}Te_{0.03}O_x$ | A | 375 | 69 | 56 | 39 |
| Comp. Ex. 3 | $Mo_{1.0}V_{0.29}Nb_{0.17}Sb_{0.01}Te_{0.21}O_x$ | A | 375 | 44 | 76 | 33 |
| Comp. Ex. 4 | $Mo_{1.0}V_{0.29}Nb_{0.17}Sb_{0.01}Te_{0.21}O_x$ | A | 375 | 57 | 91 | 52 |
| Ex. 1 | $Mo_{1.0}V_{0.29}Nb_{0.17}Sb_{0.01}Te_{0.21}O_x$ | A | 380 | 74 | 89 | 66 |
| Ex. 2 | " | B | 390 | 70 | 91 | 64 |
| Ex. 3 | $Mo_{1.0}V_{0.29}Nb_{0.17}Sb_{0.01}Te_{0.21}O_x$ (Oxalic acid treated) | B | 380 | 71 | 92 | 65 |
| Ex. 4 | $Mo_{1.0}V_{0.29}Nb_{0.17}Sb_{0.07}Te_{0.21}O_x$ | A | 480 | 70 | 88 | 62 |
| Ex. 5 | $Mo_{1.0}V_{0.29}Nb_{0.17}Sb_{0.01}Te_{0.125}O_x$ | B | 360 | 67 | 93 | 62 |
| Ex. 6 | $Mo_{1.0}V_{0.29}Nb_{0.17}Sb_{0.01}Te_{0.15}O_x$ | B | 370 | 70 | 91 | 64 |
| Ex. 7 | $Mo_{1.0}V_{0.29}Nb_{0.17}Te_{0.10}Ni_{0.042}O_x$ | A | 390 | 71 | 87 | 62 |

Comparative Example 5

Unground Catalyst

The catalyst of Example 5 is reproduced in a larger scale and also several batches are prepared, combined and used for grinding, extrusion and treatment with oxalic acid as described in Examples 8-18. The preparation procedure is as follows: In a beaker, 15.82 g of ammonium niobate (V) oxalate hydrate (20 wt % Nb content), 0.50 g of antimony oxalate and 4.0 g of oxalic acid dihydrate are mixed with 160 mL of DI water at room temperature and homogeneous solution (solution 1) is obtained. In a round bottom flask, 35.60 g of ammonium heptamolybdate tetrahydrate, 6.85 g of ammonium metavanadate and 5.80 g of telluric acid are dissolved in 200 mL water at 70° C. and a homogeneous solution (solution 2) is obtained. 5.0 mL of concentrated nitric acid is added to solution 2 and the resulting acidified solution is then combined with solution 1 and an orange-colored gel is formed. The water is removed from the gel on a rotavapor at 50° C. and a solid is obtained. This solid is further dried in an oven at 120° C. overnight and then calcined two hours in air at 275° shows 9.0 m²/g surface area. A portion of the ground powder is pressed and sized to 12-20 mesh for reactor evaluation. The rest of the powder is used for treatment with oxalic acid as described in Examples 14-18.

Example 10

Cryogenic Grinding, 5 min 10 g of the calcined solid of Comparative Example 5 are ground with a freezer/mill: five minutes for every five grams. BET analysis of the ground powder shows 16.2 m²/g surface area. The ground powder is pressed and sized to 12-20 mesh for reactor evaluation.

Example 11

Cryogenic Grinding, 10 min 110 g of the calcined solid of Comparative Example 5 are ground with a freezer/mill: ten minutes for every five grams. BET analysis of the ground powder shows 17.3 m²/g surface area. A portion of the ground powder is pressed and sized to 12-20 mesh for reactor evaluation. The rest of the powder is used for extrusion as described in Example 12.

Example 12

Extrudate 100 g of the powder catalyst from Example 11 are mixed with 28 g of Ludox AS-40. The mixture is well mixed to form a doll which is then extruded with a Loomis Ram Extruder (model #232-16) and 1.6 mm extrudates are obtained. The extrudates are dried in an oven at 120° C. overnight and then calcined in flowing $N_2$ at 500° C. for two hours. The calcined materials are cut into 2 mm in length for reactor evaluation.

Example 13

Catalyst is the same as for Example 12, but is tested at different temperature.

Table 2 summarizes the test results and BET surface areas for Examples 8-11 and test results only for Examples 12-13. All the tests are carried out under the conditions described previously and with a feed of $C_2H_6/O_2/H_2O/N_2=15/10/10/65$ molar.

TABLE 2

| Example | BET Surface Area (m²/g) | Performance | | | |
|---|---|---|---|---|---|
| | | Temp (° C.) | $C_2$ % Conv | $C_2^=$ C % Sel | $C_2^=$ C % Yield |
| Comp. Ex. 5 | 5.5 | 420 | 75 | 86 | 65 |
| Ex. 8 | 8.2 | 370 | 76 | 91 | 69 |
| Ex. 9 | 9.0 | 355 | 70 | 92 | 64 |
| Ex. 10 | 16.2 | 350 | 71 | 90 | 64 |
| Ex. 11 | 17.3 | 340 | 67 | 90 | 60 |
| Ex. 12 | | 380 | 69 | 87 | 60 |
| Ex. 13 | | 370 | 64 | 90 | 58 |

Example 14

Oxalic Acid Treatment, 1 g acid/10 g Catalyst

In a round bottom flask, 10 g of the powder catalyst of Example 9 are mixed with 1 g of oxalic acid dihydrate and 99 g of DI water. The resulting mixture is heated at 80° C. for five hours with stirring. The solid is collected by vacuum filtration and dried in an oven at 120° C. overnight. The dried solid is pressed and sized to 12-20 mesh for reactor evaluation.

Example 15

Oxalic Acid Treatment, 5 g acid/10 g Catalyst

In a round bottom flask, 10 g of the powder catalyst of Example 9 are mixed with 5 g of oxalic acid dihydrate and 95 g of DI water. The resulting mixture is heated at 80° C. for five hours with stirring. The solid is collected by vacuum filtration and dried in an oven at 120° C. overnight. The dried solid is pressed and sized to 12-20 mesh for reactor evaluation.

Examples 16-19

Oxalic Acid Treatment Followed by Annealing at 400° C.

The other portion of the dried solid of Example 15 is first pressed and sized to 12-20 mesh granules and then heated two hours at 400° C. in flowing nitrogen. The heat treated granules are evaluated at different temperatures.

Example 20

Oxalic Acid Treatment, 10 g acid/10 g Catalyst

In a round bottom flask, 20 g of the powder catalyst of Example 9 are mixed with 20 g of oxalic acid dihydrate and 180 g of DI water. The resulting mixture is heated at 80° C. for five hours with stirring. The solid is collected by vacuum filtration and dried in an oven at 120° C. overnight. A portion of the dried solid is pressed and sized to 12-20 mesh for reactor evaluation.

Examples 21-22

Oxalic Acid Treatment Followed by Annealing at 500° C.

The other portion of the dried solid of Example 20 is first pressed and sized to 12-20 mesh granules and then heated two hours at 500° C. in flowing nitrogen.

Table 3 summarizes the test results for Examples 14-22. All the tests are carried out with a feed of $C_2H_6/O_2/H_2O/N_2=15/10/10/65$ molar.

TABLE 3

| Example | BET Surface Area (m²/g) | Performance | | |
|---|---|---|---|---|
| | | Temp (° C.) | $C_2$ % Conv | $C_2^=$ % Sel | $C_2^=$ % Yield |
| Ex. 14 | 12.3 | 340 | 72 | 92 | 66 |
| Ex. 15 | 22.4 | 320 | 70 | 93 | 65 |
| Ex. 16 | 16.3 | 298 | 35 | 97 | 34 |
| Ex. 17 | 16.3 | 310 | 45 | 96 | 43 |
| Ex. 18 | 16.3 | 320 | 55 | 95 | 52 |
| Ex. 19 | 16.3 | 330 | 65 | 93 | 60 |
| Ex. 20 | 21.4 | 320 | 69 | 91 | 63 |
| Ex. 21 | 10.2 | 350 | 72 | 92 | 66 |
| Ex. 22 | 10.2 | 360 | 81 | 89 | 72 |

As described above, oxidative dehydrogenation of hydrocarbons, such as ethylene, may be performed using catalysts disclosed herein to obtain a high selectivity to the desired olefin even at high hydrocarbon conversions. For oxidative dehydrogenation of ethane to ethylene, for example, processes and catalysts disclosed herein may result in selectivities of at least 97.5 C at an ethane conversion below 20%. Other examples above show ethylene selectivity of at least 97 C % at an ethane conversion of about 20-30%; an ethylene selectivity of at least 96 C % at an ethane conversion of about 30-40%; an ethylene selectivity of at least 95 C % at an ethane conversion of about 40-50%; an ethylene selectivity of at least 93.5 C % at an ethane conversion of about 50-60%; at least 91 C % at an ethane conversion of about 60-70%, at least 88 C % at an ethane conversion of about 70-80%, and an ethylene selectivity of at least 84 C % at an ethane conversion of about 80-90%.

Advantageously, processes disclosed herein are thermodynamically favored, and may be carried out at much lower reaction temperatures (<450° C.) than steam cracking (which is generally in the range of 700-1000° C.), without the need for heat input to the reactor, and with no coke formation. The ODH production processes presented herein combine with the improved catalysts to obtain superior economics. Due to the high product selectivity and the other aspects of the process, processes disclosed herein significantly lower the net consumption of ethane feed and energy, plus significantly lower the investment cost for product separation/recovery.

The combination of the process conditions and the catalyst also result in acceptably low catalyst inventory/cost and also excellent catalyst stability and life.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the oxidative dehydrogenation of ethane to ethylene, comprising:
    contacting an ethane feed and an oxygen-containing gas in the presence of at least one of water and steam and an oxidative dehydrogenation catalyst providing selectivity to ethylene of at least 90 mole % at an ethane conversion per pass of at least 67% at a reaction temperature of 370° C. or less in an oxidative dehydrogenation reaction zone under conditions to oxidatively dehydrogenate at least a portion of the ethane to produce a product stream comprising ethylene, carbon oxides, water, and unreacted oxygen and ethane, wherein an oxygen concentration in the product stream is at least 0.1 mol %, the oxidative dehydrogenation catalyst comprising $Mo_aV_bNb_cY_dTe_eO_n$ wherein Y=Sb or Ni; a=1.0; b=0.05 to 1.0; c=0.001 to 1.0; d=0.001 to 1.0; e=0.001 to 0.5; and n is determined by the oxidation states of the other elements;
    contacting the product stream with an oxygen elimination catalyst in an oxygen elimination reaction zone to combust at least a portion of the oxygen;
    recovering from the oxygen elimination reaction zone an effluent having a reduced oxygen content;
    separating water from the effluent;
    separating carbon oxides and any non-condensable gas(es) from the ethylene and the unreacted ethane; and
    separating the ethylene from the unreacted ethane.

2. The process of claim 1, wherein the oxygen elimination catalyst comprises at least one of a combustion catalyst, an oxidation catalyst, and a hydrogenation catalyst.

3. The process of claim 1, further comprising feeding a combustible component to the oxygen elimination reaction zone.

4. The process of claim 3, wherein the added combustible compound comprises at least one of a hydrocarbon and hydrogen.

5. The process of claim 3, wherein the oxygen elimination reaction zone and the oxidative dehydrogenation reaction zone are contained in a single vessel.

6. The process of claim 1, wherein at least a portion of the ethane feed is obtained from a natural gas stream or a stream recovered from a steam cracker effluent.

7. The process of claim 1, wherein the oxygen-containing gas comprises oxygen with a purity of at least 90 mol %.

8. The process of claim 1, wherein the oxygen-containing gas comprises a mixture of oxygen and at least one inert gas.

9. The process of claim 1, further comprising recycling at least one of
    a) a portion of the separated water; and
    b) a portion of the separated ethane; to the oxidative dehydrogenation reaction zone.

10. The process of claim 1, wherein the oxidative dehydrogenation catalyst further comprises at least one catalyst selected from the group consisting of:
    a) $Mo_aV_bNb_cTe_eO_n$
        wherein for catalyst a), a=1.0; b=0.05 to 1.0; c=0.001 to 1.0, e=0.001 to 0.5, and n is determined by the oxidation states of the other elements; and
    b) $Mo_aV_bNX_cY_dZ_eM_fO_n$,
        wherein for catalyst b), X=at least one of Nb and Ta; Y=at least one of Sb and Ni; Z=at least one of the Te, Ga, Pd, W, Bi and Al; M=at least one of Fe, Co, Cu, Cr, Ti, Ce, Zr, Mn, Pb, Mg, Sn, Pt, Si, La, K, Ag and In; a=1.0; b=0.05 to 1.0; c=0.001 to 1.0; d=0.001 to 1.0; e=0.001 to 0.5; and f=0.001 to 0.3; and n is determined by the oxidation states of the other elements.

11. The process of claim 1, wherein the selectivity to ethylene is at least 92 mole % at an ethane conversion per pass of at least 67%.

12. A process for the oxidative dehydrogenation of ethane to ethylene, comprising:
    contacting ethane and an oxygen-containing gas in the presence of at least one of water and steam and a multi metal-oxide catalyst in an oxidative dehydrogenation reactor under conditions to oxidatively dehydrogenate at least a portion of the ethane to produce a product stream comprising ethylene, carbon oxides, water, and unreacted ethane;
    separating water from the product stream to recover a water fraction and a fraction comprising carbon oxides, ethylene and unreacted ethane;
    separating the fraction comprising carbon oxides, ethylene and unreacted ethane to recover carbon oxides and any non-condensable gas(es) and a hydrocarbon fraction comprising ethylene and unreacted ethane;
    separating carbon oxides and non-condensable gas(es) from the ethylene and the unreacted ethane; and
    separating the ethylene from the unreacted ethane;
    wherein the selectivity to ethylene is at least 90 mole % at an ethane conversion per pass of at least 67% at a reaction temperature of 370° C. or less, and
    wherein the multi-metal-oxide catalyst comprises $Mo_aV_bNb_cY_dTe_eO_n$, wherein Y=Sb or Ni; a=1.0; b=0.05 to 1.0; c=0.001 to 1.0; d=0.001 to 1.0; e=0.001 to 0.5; and n is determined by the oxidation states of the other elements.

13. The process of claim 12, wherein the selectivity to ethylene is at least 92 mole % at an ethane conversion per pass of at least 67%.

14. The process of claim 12, further comprising:
    contacting the product stream with an oxygen elimination catalyst in an oxygen elimination reaction zone to combust at least a portion of the oxygen;
    recovering from the oxygen elimination reaction zone an effluent having a reduced oxygen content; and
    feeding the effluent having a reduced oxygen content as the product stream fed to the separating water.

15. The process of claim 14, further comprising feeding a combustible component to the oxygen elimination reaction zone.

* * * * *